US008089628B2

(12) United States Patent
Scott et al.

(10) Patent No.: US 8,089,628 B2
(45) Date of Patent: Jan. 3, 2012

(54) PULSED-MULTILINE EXCITATION FOR COLOR-BLIND FLUORESCENCE DETECTION

(75) Inventors: Graham B. I. Scott, Houston, TX (US);
Carter Kittrell, Houston, TX (US);
Robert F. Curl, Houston, TX (US);
Michael L. Metzker, Houston, TX (US)

(73) Assignees: Baylor College of Medicine, Houston, TX (US); Rice University, Houston, TX (US)

( * ) Notice: Subject to any disclaimer, the term of this patent is extended or adjusted under 35 U.S.C. 154(b) by 0 days.

(21) Appl. No.: 12/388,358

(22) Filed: Feb. 18, 2009

(65) Prior Publication Data

US 2009/0156429 A1     Jun. 18, 2009

Related U.S. Application Data

(60) Division of application No. 11/248,910, filed on Oct. 12, 2005, now Pat. No. 7,511,811, which is a continuation of application No. 09/941,165, filed on Aug. 28, 2001, now Pat. No. 6,995,841.

(51) Int. Cl.
*G01N 21/25* (2006.01)

(52) U.S. Cl. ...................................................... 356/417

(58) Field of Classification Search .................. 356/417, 356/318; 250/458.1
See application file for complete search history.

(56) References Cited

U.S. PATENT DOCUMENTS

| | | | |
|---|---|---|---|
| 3,734,631 A * | 5/1973 | Justice et al. ................. | 356/434 |
| 4,582,788 A | 4/1986 | Erlich ............................... | 435/6 |
| 4,641,973 A * | 2/1987 | Nestler et al. ................. | 356/418 |
| 4,656,127 A | 4/1987 | Mundy ............................ | 435/6 |
| 4,683,194 A | 7/1987 | Saiki et al. ...................... | 435/6 |
| 4,683,202 A | 7/1987 | Mullis ............................ | 435/91 |
| 4,744,667 A * | 5/1988 | Fay et al. ....................... | 356/417 |
| 4,855,930 A | 8/1989 | Chao et al. .................... | 364/497 |
| 5,196,709 A | 3/1993 | Berndt et al. .............. | 250/458.1 |
| 5,233,197 A | 8/1993 | Bowman et al. ........... | 250/461.1 |
| 5,252,834 A | 10/1993 | Lin ............................. | 250/458.1 |
| 5,296,375 A | 3/1994 | Kricka et al. ................. | 435/291 |

(Continued)

FOREIGN PATENT DOCUMENTS

DE        43 38 531        5/1995

(Continued)

OTHER PUBLICATIONS

Anazawa et al., "A capillary array gel electrophoresis system using multiple laser focusing for DNA sequencing," *Anal. Chem.*, 68:2699-2704, 1996.

(Continued)

*Primary Examiner* — Kara E Geisel

(74) *Attorney, Agent, or Firm* — Fulbright & Jaworski L.L.P.

(57) ABSTRACT

The present invention provides a technology called Pulse-Multiline Excitation or PME. This technology provides a novel approach to fluorescence detection with application for high-throughput identification of informative SNPs, which could lead to more accurate diagnosis of inherited disease, better prognosis of risk susceptibilities, or identification of sporadic mutations. The PME technology has two main advantages that significantly increase fluorescence sensitivity: (1) optimal excitation of all fluorophores in the genomic assay and (2) "color-blind" detection, which collects considerably more light than standard wavelength resolved detection. Successful implementation of the PME technology will have broad application for routine usage in clinical diagnostics, forensics, and general sequencing methodologies and will have the capability, flexibility, and portability of targeted sequence variation assays for a large majority of the population.

11 Claims, 4 Drawing Sheets

U.S. PATENT DOCUMENTS

| | | | |
|---|---|---|---|
| 5,304,487 A | 4/1994 | Wilding et al. .............. 435/291 |
| 5,484,571 A | 1/1996 | Pentoney, Jr. et al. ..... 422/82.08 |
| 5,485,530 A | 1/1996 | Lakowicz et al. ............. 382/191 |
| 5,489,777 A | 2/1996 | Stedman et al. ........... 250/338.5 |
| 5,491,344 A | 2/1996 | Kenny et al. ............... 250/461.1 |
| 5,504,337 A | 4/1996 | Lakowicz et al. .......... 250/461.2 |
| 5,510,894 A * | 4/1996 | Batchelder et al. ........... 356/301 |
| 5,556,790 A | 9/1996 | Pettit .............................. 436/172 |
| 5,599,717 A | 2/1997 | Vo-Dinh ......................... 436/63 |
| 5,610,400 A * | 3/1997 | Weckstrom ................... 250/345 |
| 5,675,155 A * | 10/1997 | Pentoney et al. .......... 250/458.1 |
| 5,760,900 A * | 6/1998 | Ito et al. ........................ 436/172 |
| 5,784,157 A * | 7/1998 | Gorfinkel et al. ............. 356/318 |
| 5,846,710 A | 12/1998 | Bajaj ................................ 435/6 |
| 5,856,174 A | 1/1999 | Lipshutz et al. ........... 435/286.5 |
| 5,888,819 A | 3/1999 | Goelet et al. ...................... 435/5 |
| 5,904,824 A | 5/1999 | Oh ............................... 204/601 |
| 5,991,082 A | 11/1999 | Tsunashima et al. ......... 359/618 |
| 6,004,744 A | 12/1999 | Goelet et al. ...................... 435/5 |
| 6,013,431 A | 1/2000 | Soderlund et al. ................ 435/5 |
| 6,038,023 A | 3/2000 | Carlson et al. ................ 356/326 |
| 6,139,800 A * | 10/2000 | Chandler ................... 422/82.08 |
| 6,153,379 A | 11/2000 | Caskey et al. ...................... 435/6 |
| 6,159,686 A | 12/2000 | Kardos et al. ...................... 435/6 |
| 6,211,955 B1 | 4/2001 | Basiji et al. .................... 356/326 |
| 6,215,598 B1 | 4/2001 | Hwu .............................. 359/641 |
| 6,226,126 B1 | 5/2001 | Conemac ......................... 59/18 |
| 6,630,680 B2 | 10/2003 | Hakamata et al. .......... 250/458.1 |
| 6,903,347 B2 | 6/2005 | Baer .......................... 250/492.2 |
| 6,940,598 B2 | 9/2005 | Christel et al. ................ 356/417 |
| 2002/0113213 A1* | 8/2002 | Amirkhanian et al. .... 250/458.1 |

FOREIGN PATENT DOCUMENTS

| | | |
|---|---|---|
| JP | S60-131428 | 7/1985 |
| JP | H06-094617 | 4/1994 |
| JP | H08-512137 | 12/1996 |
| JP | H10-267844 | 10/1998 |
| JP | 2000-266666 | 9/2000 |
| JP | 2001-124627 | 5/2001 |
| JP | 2001-133405 | 5/2001 |
| WO | WO 96/23213 | 8/1996 |
| WO | WO 99/08096 | 2/1999 |
| WO | WO 99/09455 | 2/1999 |

OTHER PUBLICATIONS

Barany, "Genetic disease detection and DNA amplification using cloned thermostable ligase," *Proc. Natl. Acad. Sci. USA*, 88:189-193, 1991.

Brenner et al., "Gene expression analysis by massively parallel signature sequencing (MPSS) on microbead arrays," *Nat Biotechno.*, 18:630-634, 2000.

Brenner et al., "In vitro cloning of complex mixtures of DNA on microbeads: physical separation of differentially expressed cDNAs," *PNAS*, 97(4):1665-1670, 2000.

Cohen et al., "Separation and analysis of DNA sequence reaction products by capillary gel electrophoresis," *J. Chromatogr.*, 516:49-60, 1990.

Crabtree et al., "Construction and evaluation of a capillary array DNA sequencer based on a micromachined sheath-flow cuvette," *Electrophoresis*, 21:1329-1335, 2000.

Deeb et al., "A Pro12A1a substitution in PPARγ2 associated with decreased receptor activity, lower body mass index and improved insulin sensitivity," *Nature Genet.*, 20:284-287, 1998.

Drossman et al., "High-speed separations of DNA sequencing reactions by capillary electrophoresis," *Anal. Chem.*, 62:900-903, 1990.

Effenhauser, et al "High-speed separation of antisense oligonucleotides on a micromachined capillary electrophoresis device," *Anal. Chem.*, 66:2949-2953, 1994.

Effenhauser, et al. "Glass chips for high-speed capillary electrophoresis separations with submicrometer plate heights," *Anal. Chem.*, 65:2637-2642, 1993.

Harrison et al., "Micromachining a miniaturized capillary electrophoresis-based chemical analysis system on a chip," *Science*, 261:895-897, 1993.

Huang et al., "Bias in quantitative capillary zone electrophoresis caused by electrokinetic sample injection," *Anal. Chem.*, 60:375-377, 1988.

Huang et al., "Capillary array electrophoresis using laser-excited confocal fluorescence detection: an approach to high-speed, high-throughput DNA sequencing," *Anal Chem.*, 64:967-972, 1992.

Huang et al., "DNA sequencing using capillary array electrophoresis," *Anal. Chem.*, 64: 2149-2154, 1992.

Ju et al., "Fluorescence energy transfer dye-labeled primers for DNA sequencing and analysis," *Proc. Natl. Acad. Sci. U S A.*, 92:4347-4351, 1995.

Kambara and Takahashi, "Multiple-sheathflow capillary array DNA analyser," *Nature*, 361: 565-566, 1993.

Karger et al., "Multiwavelength fluorescence detection for DNA sequencing using capillary electrophoresis," *Nucleic Acids Res.*, 19:4955-4962, 1991.

Kheterpal et al., "DNA sequencing using a four-color confocal fluorescence capillary array scanner," *Electrophoresis*, 17:1852-1859, 1996.

Kornher and Livak "Mutation detection using nucleotide analogs that alter electrophoretic mobility," *Nucleic Acids Res.*, 17(19):7779-7784, 1989.

Kuppuswamy et al., "Single nucleotide primer extension to detect genetic diseases: Experimental application to hemophilia B (factor IX) and cystic fibrosis genes," *Proc. Natl. Acad. Sci. U.S.A.*, 88:1143-1147, 1991.

Kurg et al., "Arrayed primer extension: solid-phase four-color DNA resequencing and mutation detection technology." *Genet Testing*, 4(1):1-7, 2000.

Landegren et al., "A ligase-mediated gene detection technique," *Science*, 241:1077-1080, 1988.

Lee and Anvret. "Identification of the most common mutation within the porphobilinogen deaminase gene in Swedish patients with acute intermittent porphyria," *Proc Natl Acad Sci USA.*, 88:10912-10915, 1991.

Lieberwirth et al., "Multiplex dye DNA sequencing in capillary gel electrophoresis by diode laser-based time-resolved fluorescence detection," *Anal Chem.*, 70:4771-4779, 1998.

Livak and Hainer. "A microtiter plate assay for determining apolipoprotein E genotype and discovery of a rare allele," *Hum Mutat.*, 3:379-385, 1994.

Lu and Yeung. "Optimization of excitation and detection geometry for multiplexed capillary array electrophoresis of DNA fragments," *Appl. Spectrosc.*, 49(5): 605-609, 1995.

Luckey et al., "High speed DNA sequencing by capillary electrophoresis," *Nucleic Acids Res.*, 18(15):4417-4421, 1990.

Luryi, CRISP Abstract: Grant No. 5R01HG01487-05. 4 Color automated DNA sequencing machine with asynchronous network operation, Apr. 1996-Jun. 2002.

Madabhushi, "Separation of 4-color DNA sequencing extension products in noncovalently coated capillaries using low viscosity polymer solutions," *Electrophoresis* 19:224-230, 1998.

Manz, et al., "Planar chips technology for miniaturization and integration of separation techniques into monitoring systems," *J. Chromatogr.*, 593:253-258, 1992.

Meaburn, "Signal to noise ratios-the principal criteria of merit," In: *Detection and Spectrometry of Faint Light*, Reidel, Dordrecht, Holland, 246-266, 1976.

Metzker et al., "Electrophoretically uniform fluorescent dyes for automated DNA sequencing," *Science*, 271:1420-1422, 1996.

Metzker et al., "Termination of DNA synthesis by novel 3'-modified-deoxyribonucleoside 5'-triphosphates," *Nucleic Acids Res.*, 22:4259-4267, 1994.

Nickerson et al., "Automated DNA diagnostics using an ELISA-based oligonucleotide ligation assay," *Proc Natl Acad Sci USA.*, 87:8923-8927, 1990.

Nikiforov et al., "Genetic Bit Analysis: a solid phase method for typing single nucleotide polymorphisms," *Nucleic Acids Res.*, 22(20):4167-4175, 1994.

Nyren et al., "Solid phase DNA minisequencing by an enzymatic luminometric inorganic pyrophosphate detection assay," *Anal. Biochem.*, 208:171-175, 1993.

Office Action, issued in U.S. Appl. No. 09/941,165, mailed Sep. 4, 2005.
Office Action, issued in U.S. Appl. No. 09/941,165, mailed Feb. 20, 2004.
Office Action, issued in U.S. Appl. No. 09/941,165, mailed Sep. 22, 2004.
Office Action, issued in U.S. Appl. No. 11/248,910, mailed May 11, 2007.
Office Action, issued in U.S. Appl. No. 11/248,910, mailed Jan. 30, 2008.
Prezant and Fischel-Ghodsian. "Trapped-oligonucleotide nucleotide incorporation (TONI) assay, a simple method for screening point mutations," *Hum Mutat.*, 1:159-164, 1992.
Prober et al., "A system for rapid DNA sequencing with fluorescent chain-terminating dideoxynucleotides," *Science*, 238:336-341, 1987.
Quesada and Zhang "Multiple capillary DNA sequencer that uses fiber-optic illumination and detection," *Electrophoresis*, 17:1841-1851, 1996.
Quesada et al., "Multi-capillary optical waveguides for DNA sequencing," *Electrophoresis*, 19:1415-1427, 1998.
Ronaghi et al., "A sequencing method based on real-time pyrophosphate," *Science*, 281:363, 365, 1998.
Rosenblum et al., "New dye-labeled terminators for improved DNA sequencing patterns," *Nucleic Acids Res.*, 25:4500-4504, 1997.
Sambrook et al., "Molecular Cloning," *A Laboratory Manual, 2d Ed.*, Cold Spring Harbor Laboratory Press, New York, 13.7-13.9:1989.
Shibata et al., "RIKEN integrated sequence analysis (RISA) system-384-format sequencing pipeline with 384 multicapillary sequencer," *Genome Res.* 10:1757-1771, 2000.
Shumaker et al., "Mutation detection by solid phase primer extension," *Hum Mutat.*, 7:346-354, 1996.
Smith et al., "Fluorescence detection in automated DNA sequence analysis," *Nature*, 321(6071):674-679, 1986.
Sokolov, "Primer extension technique for the detection of single nucleotide in genomic DNA," *Nucleic Acids Res.*, 18(12):3671, 1990.
Sweedler et al., "Fluorescence detection in capillary zone electrophoresis using a charge-coupled device with time-delayed integration," *Anal. Chem.*, 63:496-502, 1991.
Swerdlow and Gesteland, "Capillary gel electrophoresis for rapid, high resolution DNA sequencing," *Nucleic Acids Res.*, 18(6): 1415-1419, 1990.
Swerdlow et al., "Capillary gel electrophoresis for DNA sequencing. Laser-induced fluorescence detection with the sheath flow," *J Chromatogr.*, 516:61-67, 1990.
Swerdlow et al., "Three DNA sequencing methods using capillary gel electrophoresis and laser-induced fluorescence," *Anal Chem.*, 63:2835-2841, 1991.
Syvanen et al., "A primer-guided nucleotide incorporation assay in the genotyping of Apolipoprotein E," *Genomics*, 8:684-692, 1990.
Takahashi et al., "Multiple sheath-flow gel capillary-array electrophoresis for multicolor fluorescent DNA detection," *Anal. Chem.*, 66:1021-1026, 1994.
Taylor and Yeung, "Multiplexed fluorescence detector for capillary electrophoresis using axial optical fiber illumination," *Anal. Chem.*, 65: 956-960, 1993.
Tsuda et al., "Rectangular capillaries for capillary zone elctrophoresis," *Anal. Chem.*, 62:2149-2152, 1990.
Ueno and Yeung, "Simultaneous monitoring of DNA fragments separated by electrophoresis in a multiplexed array of 100 capillaries," *Anal. Chem.*, 66:1424-1431, 1994.
Wei and Hemmings, "The NOTCH4 locus is associated with susceptibility to schizophrenia," *Nature Genet.*, 25:376-377, 2000.
Woolley and Mathies, "Ultra-high-speed DNA fragment separations using microfabricated capillary array electrophoresis chips," *Proc Natl Acad Sci U S A*, 91:11348-11352 1994.
Yeo et al., "A frameshift mutation in MC4R associated with dominantly inherited human obesity," *Nature Genet.*, 20:111-112, 1998.
Zagursky and McCormick, "DNA sequencing separations in capillary gels on a modified commercial DNA sequencing instrument," *Biotechniques*, 9(1): 74-79, 1990.
Zhang et al., "A multiple-capillary electrophoresis system for small-scale DNA sequencing and analysis," *Nucleic Acids Res.*, 27(24):e36, i-vii, 1999.
Office Communication issued in Japanese Patent Application No. 2003-525245, dispatch date Jun. 8, 2009 (English translation).
Office Communication, issued in Canadian Patent Application No. 2,484,336, dated Feb. 24, 2010.
Office Communication, issued in Japanese Patent Application No. 2003-525245, dated May 14, 2008. (English translation).
Office Communication, issued in Japanese Patent Application No. 2008-291646, dated May 30, 2011. (English translation).
Office Communication, issued in Japanese Patent Application No. 2010-227285, dated Dec. 1, 2010. (English translation).
Supplementary European Search Report, issued in European Application No. EP 02 75 7433, issued Mar. 31, 2011.
Office Communication, issued in Japanese Patent Application No. 2010-227285, dated Aug. 22, 2011.

* cited by examiner

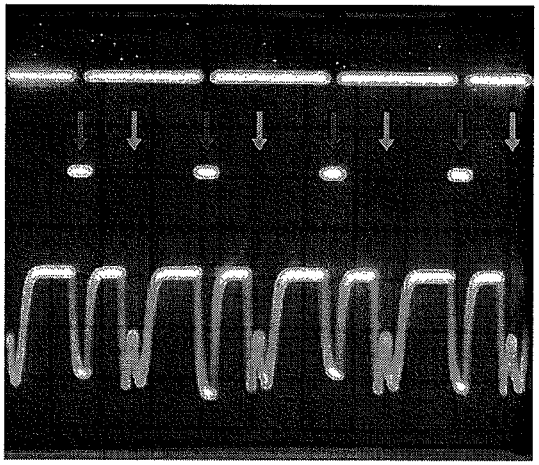
FIG. 4A
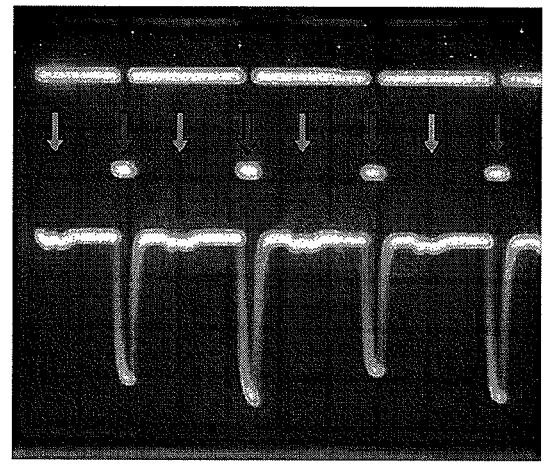
FIG. 4B
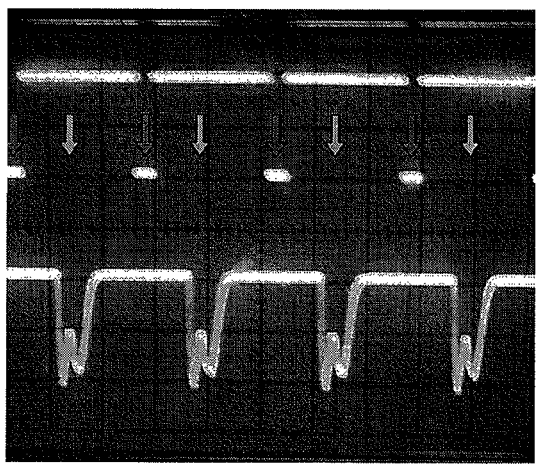
FIG. 4C
FIG. 4

PULSED-MULTILINE EXCITATION FOR COLOR-BLIND FLUORESCENCE DETECTION

CROSS REFERENCE TO RELATED APPLICATION

This application is a divisional of U.S. patent application Ser. No. 11/248,910, filed Oct. 12, 2005, now U.S. Pat. No. 7,511,811 which is a continuation of U.S. patent application Ser. No. 09/941,165, filed Aug. 28, 2001, which issued as U.S. Pat. No. 6,995,841 on Feb. 7, 2006, the contents of which applications are incorporated herein by reference in their entirety.

BACKGROUND OF THE INVENTION

I. Field of the Invention

The present invention relates generally to the fields of high throughput genetic analysis applications and fluorescence spectroscopy. More particularly, it provides a variety of compositions and methods for use in high-throughput DNA sequence identification.

II. Description of Related Art

The Human Genome Project (HGP) holds tremendous promise for discoveries of the molecular mechanisms that trigger the onset of many common diseases over the next several decades. The initial HGP goals underway will provide or have provided the complete and accurate genome sequences of human and multiple well-studied genetic model organisms, such as mouse, rat, fruit fly, nematode, yeast and numerous bacteria. From this foundation of reference genome sequences, the elucidation of complete gene sets, coupled with comparative cross-species studies, are expected to assist significantly in the assignment to specific human genes of protein function and disease associations. Other technologies complement the assignment of biological functions: gene and protein expression profiling, mouse gene-knockouts, and techniques that measure protein-protein interactions. The elucidation of gene structure-protein function relationships are key to understanding how genomic sequence variation between individuals can cause increased risk or predisposition to certain complex diseases or are even the etiologic agents responsible for the onset of particular diseases. However, the use of genetic variation in clinical practice is only beginning and technology to facilitate its use is greatly needed.

The most commonly observed form of human sequence variation is single nucleotide polymorphisms (SNPs), which occur at a frequency of approximately 1-in-300 to 1-in-1000 base pairs. In general, 10%-to-15% of SNPs will affect either protein function by altering specific amino acid residues, or will affect the proper processing of genes by changing splicing mechanisms, or will affect the normal level of expression of the gene or protein by varying regulatory mechanisms. Several recent examples are the associations of mutations with the NOTCH4 gene and schizophrenia (Wei et al., 2000), peroxisome proliferator-activated receptor gamma (PPARγ) gene and severe insulin resistance (Deeb et al., 1998), and melanocortin-4 receptor (MC4R) gene and inherited obesity (Yeo et al., 1998).

The identification of informative SNPs will lead to more accurate diagnosis of inherited diseases, better assessment of risk susceptibilities, and could be assayed in specific tissue biopsies for sporadic mutations. An individual's SNP profile could be used to offset and significantly delay the progression of disease by helping in the choice of prophylactic drug therapies. A SNP profile of drug metabolizing genes could be used to prescribe a specific drug regimen to provide safer and more efficacious results. To accomplish goals like these, genome sequencing will move into the resequencing phase of not just a handful of individuals, but potentially the partial sequencing of most of the population. Resequencing simply means sequencing in parallel specific regions or single nucleotides that are distributed throughout the human genome to obtain the SNP profile for a given complex disease.

For this technology to be applicable and practicable for routine usage in medical practice, it must be robust, easy-to-use, highly sensitive, flexible, portable, and the results should be accurate and rapidly obtained. While current technologies at large genome centers are robust and results are accurate, they are inadequate and inflexible for resequencing millions of individuals in routine clinical practice. It is therefore advantageous to develop a DNA sequencing instrument, which meets these needs. Miniaturization of this technology is also advantageous because smaller instruments potentially require less sample and reagents and can be more readily transported and located in areas such as clinics or doctors' offices.

Ideally, DNA sequencing technology would have the sensitivity for direct assays without DNA amplification, and be simple and portable for routine usage in basic, applied, and clinical laboratories. Currently, DNA sequencing technology for high-throughput analyses are specialized and centralized in large genome centers and require numerous molecular biology manipulations that take days or weeks of preparation before DNA sequence analysis can be performed. Thereafter, the state-of-the-art technology involves the attachment of four different fluorescent dyes or fluorophores to the four bases of DNA (i.e., A, C, G, and T) that can be discriminated by their respective emission wavelengths, the electrophoretic separation of the nested set of dye-labeled DNA fragments into base-pair increments, and the detection of the dye fluorescence following irradiation by a single argon-ion laser source. Current instrumentation for electrophoretic separation comprises a 96-capillary array that disperses the different fluorescent signals using a prism, diffraction grating, spectrograph, or other dispersing element and images the four colors onto a charged-coupled device (CCD) camera. The throughput of each 96-capillary instrument is approximately 800 DNA samples per day, and the success of the HGP in large-scale genomic sequencing has been attributed to the use of hundreds of these machines throughout the world. The main disadvantages of the current technology are the laborious cloning or amplification steps needed to provide sufficient DNA material for analyses, the relatively large size of the instruments (roughly the size of a 4-foot refrigerator), and the inadequate sensitivity of detection (i.e., inefficient excitation of fluorescent dyes with absorption maxima far from the laser excitation wavelength).

Although the resolution of spectral emission wavelengths is the mainstream technology used in commercial and academic prototype instruments, several groups have explored other physical properties of fluorescence as a method for discriminating multicolor systems for DNA sequence determination. Recently, Lieberwirth et al. (1998) described a diode-laser based time-resolved fluorescence confocal detection system for DNA sequencing by capillary electrophoresis. In this system, a semiconductor laser (630 nm) was modulated using a tunable pulse generator at a repetition rate of 22 MHz (454 psec pulses) and focused by a microscope objective. The fluorescence was collected by the same objective and imaged on a single photon counting module APD (Lieberwirth et al., 1998).

The Luryi group at SUNY Stony Brook have proposed a multiple laser excitation approach using different radio frequency (RF) modulations and demodulations to discriminate a mixture of fluorophores (U.S. Pat. Nos. 5,784,157 and 6,038,023). U.S. Pat. No. 5,784,157 describes a 4-laser based fiber optic single capillary monitoring device, which initially has a non-wavelength component, but later the invention discusses the coupling of spectral resolution for fluorophore discrimination. There are three significant flaws apparent in this system relating to the enhanced fluorescence cross-talk and laser scattered light, low sensitivity detection, and a system that does not appear to scale beyond one capillary.

As described, the target capillary is illuminated simultaneously by all four lasers, which are modulated by different RF signals. The different RF signals for all of the dyes are summed together and the detector photodiodes are demodulated by additional heterodyne RF signals. Interestingly, Gorfinkel and Luryi describe the creation of Bragg reflectors to eliminate cross-talk modulation for a given dye set. Fluorescence cross-talk, however, will not be eliminated using this technique. Signal from the "wrong" dye, which is weakly excited off-resonance by a particular laser, will be encoded with the corresponding "wrong" frequency, decoded, and added to the signal for the target dye. Moreover, scattered laser light will also be modulated, and is likewise not rejected by the heterodyne detection.

The simultaneous multi-modulation method also has a serious shortcoming for the detection of low light levels, which is a specific aim of the current invention. All the lasers are proposed to operate simultaneously, followed by detection of substantially all of the entire fluorescence, and conversion of the collected fluorescence to an electrical signal. This design potentially creates a correspondingly high quantum statistical noise level, which should be distributed to all the detectors. The demultiplexing process of RFs does not remove this excessive random noise, even if the corresponding signal is small (Meaburn, 1976). In comparison, the Pulse-Multiline Excitation (PME) system described in the current invention exhibits noise levels in proper proportion, so that a weak signal originating from a particular laser pulse has a correspondingly low detected noise level during that laser's sub-cycle. Optimizing the optical system for producing low noise levels is essential in establishing the optimum contrast between the presence and absence of a given dye.

Finally, U.S. Pat. No. 5,784,157 describes a rather complicated array of optical fibers, combiners, splitters, and 4 heterodyne detectors with their associated spectral filters for a single capillary channel. Scaling this system to a 2-capillary system would entail doubling the mentioned detector components. Unfortunately a CCD camera is not readily adapted for high frequency RF modulation, as it is an "inherently discrete-time" device. In a more recent document. U.S. Pat. No. 6,038,023, the multiplicity of spectral filters has been replaced with a dispersing prism spectrometer and a high speed one dimensional array detector for use with a single capillary channel device; the potential to scale up to a capillary array system is more feasible as discussed by the Luryi group, but may require a multiplicity of such spectrometer units.

The current invention comprises a novel fluorescence device, which is capable of significant improvements in the limit of detection of multi-color fluorescence reactions and may be applied to direct measurement of such reactions from biological sources (i.e., without the need for PCR or cloning amplifications). Moreover, this technology, called Pulse-Multiline Excitation or "PME" can be configured on a small work surface or in a small instrument, compared to the current DNA sequencing instruments. Thus, a DNA sequencer the size of a suitcase or smaller is described.

The development of improved DNA sequencing chemistries will likely improve the number of independent assays that can be run in parallel. This technology will have broad application in both general sequencing and forensic applications.

SUMMARY OF THE INVENTION

Thus, the present invention contemplates an apparatus and method for use in high-throughput DNA sequence identification. An aspect of the invention is a pulse-multiline excitation apparatus for analyzing a sample containing one or more fluorescent species, comprising: one or more lasers configured to emit two or more excitation lines, each excitation line having a different wavelength; a timing circuit coupled to the one or more lasers and configured to generate the two or more excitation lines sequentially according to a timing program to produce time-correlated fluorescence emission signals from the sample; a non-dispersive detector positioned to collect the time-correlated fluorescence emission signals emanating from the sample; and an analyzer coupled to the detector and configured to associate the time-correlated fluorescence emission signals with the timing program to identify constituents of the sample.

The detector and the analyzer may be integral. In one embodiment, the two or more excitation lines intersect at the sample, or the two or more excitation lines may be configured so that they do not intersect in the sample. The two or more excitation lines may be coaxial.

In one embodiment of the invention, the apparatus may further comprise an assembly of one or more prisms in operative relation with the one or more lasers and configured to render radiation of the two or more excitation lines substantially colinear and/or coaxial.

The apparatus may have 1, 2, 3, 4, 5, 6, 7, 8, 9, 10, 11, 12, 13, 14, 15, 16 or more excitation lines having 1, 2, 3, 4, 5, 6, 7, 8, 9, 10, 11, 12, 13, 14, 15, 16 or more excitation wavelengths, respectively. The sample may be comprised in 1, 2, 3, 4, 5, 6, 7, 8, 9, 10, 11, 12, 13, 14, 15, 16, up to 20, up to 24, up to 28, up to 36, up to 48, up to 64, up to 96, up to 384 or more capillaries. A sheath flow cuvette may be used.

The timing program may comprise a delay between the firing of each laser of between about 10 fs and about 5 s, between about 1 ms and about 100 ms, or between about 50 ps and about 500 ps. One or more of the excitation lines is pulsed. The pulsed excitation line may be controlled by transistor-transistor logic (TTL) or by mechanical or electronic means. In one embodiment, the apparatus may generate a sequence of discrete excitation lines that are time-correlated with the fluorescence emission signals from the sample.

The lasers may independently comprise a diode laser, a semiconductor laser, a gas laser, such as an argon ion, krypton, or helium-neon laser, a diode laser, a solid-state laser such as a Neodymium laser which will include an ion-gain medium, such as YAG and yttrium vanadate ($YVO_4$), or a diode pumped solid state laser. Other devices, which produce light at one or more discrete excitation wavelengths, may also be used in place of the laser. The laser may further comprise a Raman shifter in operable relation with at least one laser beam. In one embodiment of the invention, the excitation wavelength provided by each laser is optically matched to the absorption wavelength of each fluorophore.

The detector may comprise a charged couple device, a photomultiplier tube, a silicon avalanche photodiode or a silicon PIN detector. The footprint of the device is preferably small, such as less than 4 ft×4 ft×2 ft, less than 1 ft×1 ft×2 ft, and could be made as small as 1 in×3 in×6 in.

Another aspect of the current invention comprises a method of identifying sample components comprising: (a) preparing a sample comprising sample components, a first dye and a second dye; (b) placing the sample in the beam path of a first excitation line and a second excitation line; (c) sequentially firing the first excitation line and the second excitation line; (d) collecting fluorescence signals from the samples as a function of time; and (e) sorting the fluorescence by each excitation line's on-time window, wherein the sample components are identified. It is an aspect of the invention that the fluorescence signals are collected from discrete time periods in which no excitation line is incident on the sample, the time periods occurring between the firing of the two excitation lines. This technique is known as "looking in the dark." Yet another aspect of the present invention is that the absorption maximum of the first dye substantially corresponds to the excitation wavelength of the first excitation line. The absorption maximum of the second dye may also substantially corresponds to the excitation wavelength of the second excitation line. In yet another aspect of the current invention there is a third and fourth dye and a third and fourth excitation line, wherein the absorption maxima of the third and fourth dyes substantially correspond to the excitation wavelengths of the third and four excitation lines, respectively. Similarly, there may be 5, 6, 7, 8, 9, 10, 11, 12, 13, 14, 15, 16 or more dyes wherein the absorption maxima of the dyes substantially corresponds to excitation wavelengths of a $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, or more excitation lines, respectively. The dyes may be a zanthene, fluorescein, rhodamine, BODIPY, cyanine, coumarin, pyrene, phthalocyanine, phycobiliprotein, Alexa, squariane dyes, or some other suitable dye.

In one embodiment of the current invention, the sample components enable the determination of SNPs. The method may be for the high-throughput identification of informative SNPs. The SNPs may be obtained directly from genomic DNA material, from PCR amplified material, or from cloned DNA material and may be assayed using a single nucleotide primer extension method. The single nucleotide primer extension method may comprise using single unlabeled dNTPs, single labeled dNTPs, single 3'-modified dNTPs, single base-modified 3'-dNTPs, single alpha-thio-dNTPs or single labeled 2',3'-dideoxynucleotides. The mini-sequencing method may comprise using single unlabeled dNTPs, single labeled dNTPs, single 3'-modified dNTPs, single base-modified 3'-dNTPs, single alpha-thio-dNTPs or single labeled 2',3'-dideoxynucleotides. The SNPs may be obtained directly from genomic DNA material, from PCR amplified material, or from cloned DNA materials and may be assayed using Sanger sequencing.

In another embodiment of the current invention, analyzing the signals is adapted for the accurate diagnosis of inherited disease, better prognosis of risk susceptibilities, identification of sporadic mutations, or prescribing tailor-made daily drug regimens for individual patients. Analyzing the signals may be adapted for routine usage in clinical diagnostics, forensics applications or determining general sequencing methodologies.

Yet another aspect of the current invention is a method of identifying sample components comprising: (a) obtaining a biological sample; (b) labeling said sample with one or more fluorophores; (c) separating components of said sample; and (d) detecting said sample components with a device wherein said device may comprise: one or more lasers configured to emit two or more excitation lines, each excitation line having a different excitation wavelength; a timing circuit coupled to the one or more lasers and configured to fire the two or more excitation lines sequentially according to a timing program to produce time-correlated fluorescence emission signals from the sample; and a non-dispersive detector positioned to collect the time-correlated fluorescence emission signals; wherein said detector collects time correlated data from said sample comprising fluorescent emissions of the sample as a result of irradiation by the one or more excitation lines.

The sample components may be nucleic acids, amino acids or proteins. The separation may be by electrophoresis, chromatography or mass spectrometry (MS) such as MALDI-TOF, quadrapole mass filter or magnetic sector MS. The sample components may be addressed on high density chip arrays.

In one embodiment, the method may further comprise: (e) contacting said sample components on a surface comprising immobilized oligonucleotides at known locations on said surface; and (f) performing a single nucleotide incorporation assay or a mini-sequencing assay. In yet another embodiment, the method may further comprise rastering said surface or said excitation lines such that said excitation lines contact said surface at multiple locations.

Another aspect of the current invention is a device comprising: (a) one or more lasers having two or more excitation lines; (b) one or more beam steering mirrors wherein said excitation lines each strike said mirrors; (c) a first prism, wherein said two or more excitation lines strike one surface and exit from a second surface of said first prism; and (d) a second prism at an angle relative to said first prism, wherein said two or more excitation lines strike one surface of said second prism after exiting said first prism and exit said second prism, wherein said two or more excitation lines are substantially colinear and/or substantially coaxial after exiting said second prism. The angle of the second prism relative to the first prism is dependent on the optical material used. For example, for high dispersion flint glass, the two prisms will be arranged such that the second prism is angled at 45° relative to the first prism. For quartz, the angular displacement ranges from 30° to 50°.

Another aspect of the current invention comprises a method of illuminating a sample comprising: (a) steering two or more excitation lines onto a first surface of a first prism; (b) steering two or more excitation lines from the second surface of said first prism to a first surface of a second prism; wherein said second prism is angled about 45° from said first prism; (c) steering said two or more excitation lines onto a sample after exiting second surface of said second prism, wherein said two or more excitation lines are substantially colinear and/or substantially coaxial after exiting said second prism.

Yet another aspect of the current invention comprises a method of controlling a sequence of excitation lines comprising: (a) obtaining a TTL circuit comprising an electronic stepper wherein said circuit is operationally connected to one or more lasers having two or more excitation lines; (b) and controlling the sequential firing of the one or more lasers having two or more excitation lines with a clock pulse from the circuit, wherein the frequency of firing one laser is equivalent to the frequency of firing a second laser, but phased shifted so that one or more lasers having two or more excitation lines can be sequentially pulsed. The cycle time of one clock pulse may be from 1 μsecond to 5 seconds, or from 100 μsecond to 1 second. The length of time a first laser produces an excitation line may be similar to the length of time a second laser produces an excitation line. As used herein, similar means within 20%, within 10%, or more preferably within 5% of the time length. Between 2-to-16, or 2-to-8 excitation lines are sequentially pulsed.

Yet another method of the current invention comprises a method of controlling a sequence of excitation lines comprising: (a) obtaining a TTL circuit comprising an electronic stepper wherein said circuit is operationally connected to one or more lasers having two or more excitation lines; (b) and controlling the sequential firing of the one or more lasers having two or more excitation lines with a clock pulse from the circuit, wherein the frequency of firing a first laser is different from the frequency of firing a second laser. This method may be used to control 2, 3, 4, 5, 6, 7, 8, 9, 10, 11, 12, 13, 14, 15 or 16 lasers.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A, FIG. 4B and FIG. 4C. Photographic data from the oscilloscope output. Two channels from the oscilloscope were set to record the clock signal for firing the red laser (top line) and the PMT detector output (bottom line). Arrows correspond to the red and green laser pulses. Data on dilute aqueous solutions containing both BODIPY 523/547 and BODIPY 630/650 dyes (FIG. 4A), BODIPY 630/650 dye only (FIG. 4B), or BODIPY 523/547 dye only (FIG. 4C) were collected.

DESCRIPTION OF ILLUSTRATIVE EMBODIMENTS

I. The Present Invention

Figure 1:
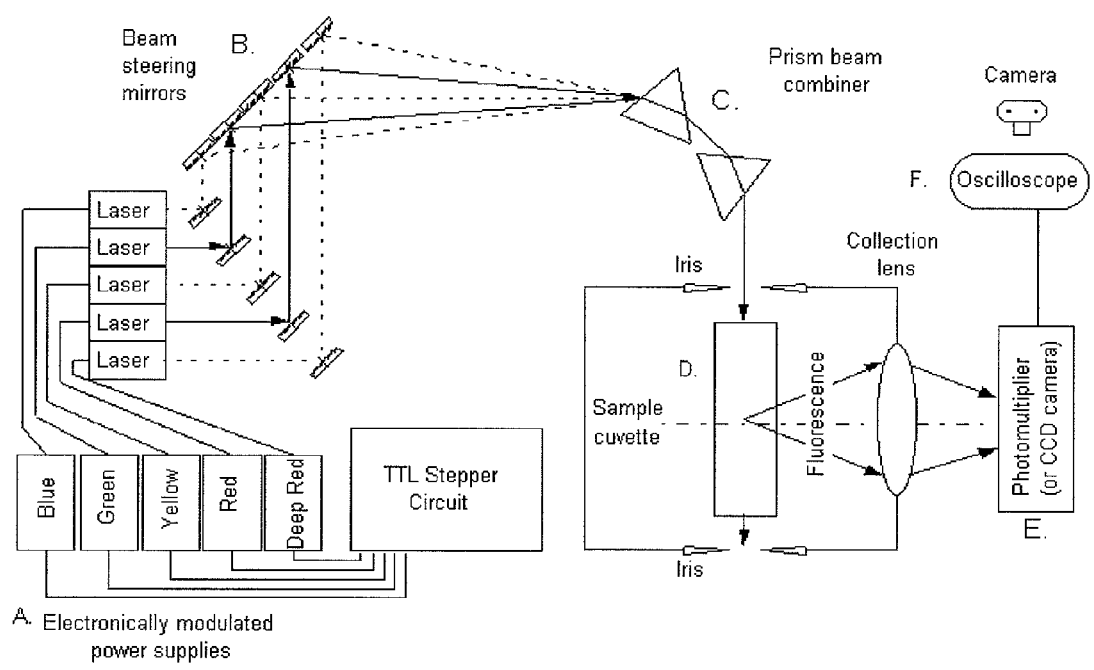
FIG. 1. An example of a PME device where each laser is regulated individually by its own power supply (A). The TTL stepper or clock chip circuit (FIG. 3) chooses which power supply is turned on at a specific time as it cycles through the five lasers. The beam steering mirrors (B) allow various degrees of adjustment to align the excitation lines so that once they go through a dual prism assembly (FIG. 2) (C), they will become colinear and/or coaxial. The beams enter the dark box (D) where scattered light is reduced by the use of irises and a long cell. The dyes are detected by the photomultiplier tube (E) through a collecting lens. The signals are recorded by the oscilloscope (F) where digital pictures can be analyzed.

The present invention describes a novel device and approach to fluorescence detection, which has general application for genetic analysis methodologies with particular emphasis on DNA sequencing technologies and high-throughput identification of single nucleotide polymorphisms (SNPs). The PME technology has two main advantages that significantly increase fluorescence sensitivity: optimal excitation of all fluorophores in the genomic assay and "color-blind" detection, which collects considerably more light than traditional dispersive detectors. The fluorescence detector can be designed to miniaturize DNA sequencing technology with a sensitivity enabling direct detection of fluorescent DNA assays from genomic DNA material. The PME is useful for clinical diagnostic, forensic, and general sequencing.

II. Pulsed Multi-Line Excitation (PME) Detection

In the current invention, spectral dispersion or wavelength discrimination of fluorescent dyes is eliminated, which increases the amount of fluorescent signal detected. The sequential pulsed-laser excitation system using multiple lasers emitting specific wavelengths of light, which are matched for efficient excitation of a given set of fluorophores, can determine selectivity and sensitivity. By matching the absorption maximum of each fluorophore, the PME technology excites each dye with the highest quantum efficiency, thus considerably reducing the required sample size (i.e., the number of fluorescent molecules required for detection). At first glance, replacing one laser with four lasers may appear counterintuitive to miniaturization. New solid state lasers, however, such as diode pumped Nd:YAG sources or diode lasers are much smaller (ca. 2" long) than standard argon ion lasers and are much more efficient requiring smaller power supplies for operation. For example, the footprint of four solid-state lasers together is approximately 20-fold smaller than a single argon-ion laser system. Simply replacing the argon-ion laser, which for a DNA sequencer relies on two excitation lines at 488 nm and 514.5 nm, with a equal power 532 nm Nd:YAG can reduce the laser size, but would reduce the excitation/emission intensities of shorter wavelength dyes, and still would not efficiently excite longer-wavelength dyes that have absorption maxima far from the laser wavelengths.

For the PME technology to discriminate four fluorescent dyes, four excitation lines are combined by inverse dispersion, which is illustrated but not limited to using a prism assembly or diffraction grating. The resultant beam would look on average like a "white light" laser beam. However, the solid-state lasers are electronically controlled and are pulsed or fired sequentially as discrete packages of wavelength specific light. Alternatively, laser sources can be pulsed or fired using a synchronized shutter system. Each dye brightly fluoresces when its matched laser source is turned on, while it responds only weakly, if at all, to the other three laser pulses. The fluorescence from each excitation event is collected using a non-dispersed or "color blind" method of detection. A non-dispersive detector is a detector in which the incident radiation is not separated based on the emission fluorescence wavelength of different fluorescent dyes. Thus, DNA sequence is determined by the PME technology based on the time correlation of detector response to specific wavelengths of excitation light, and not spectral resolution of emission wavelengths. Switching the solid-state lasers on a millisecond timescale is straightforward, hence thousands of 4-laser excitation cycles may be completed in the time scale for eluting a single base of DNA by capillary electrophoresis.

Moreover, an advantage of the non-dispersed system is that the detector (i.e., CCD) collects significantly more light, since the fluorescent light is directly coupled to the detector. Typically for the current DNA sequencer, a dispersive element requires highly collimated light for effective wavelength separation. Moving the collection lens closer to the sample can increase the collected fluorescent light, but collimation is lessened, and spectral selectivity is reduced. Similarly, reducing the distance between the dispersing element and the detector results in reduced spectral selectivity. For the non-dispersed system, however, moving the collection lens much closer to the sample or to the detector increases the collected light, inverse to the square of the distance, but without sacrificing the selectivity that is provided by four laser cycling. Thus, the miniaturization process inherently delivers more fluorescent light to the detector.

Typically, miniaturizing a system incurs inevitable penalties in sensitivity and selectivity. For example, fluorescent signal is lost as the laser source becomes smaller in size and power, and selectivity is compromised because spectral dispersing elements need physical space to separate emission wavelengths and compressing the spectrometer portion of the detection sacrifices spectral resolution. Consequently, the sample size is increased to offset these losses, which tends to marginalize the benefits derived by shrinking the conventional dispersive optical system. The design described herein minimizes the losses in downsizing instrumentation, but increases the sensitivity considerably by the process of miniaturization. The current invention comprises a novel detection system that allows the optical components to act synergistically when miniaturized.

An additional advantage of non-dispersed detection is enhanced signal-to-noise compared to the current 96-capillary DNA sequencer. To obtain the wavelength spectrum for each DNA sequence reaction, a large number of pixels are read out, and this electronic readout process adds noise for every pixel read. For the non-dispersed system, all pixels that receive light from a particular capillary are "binned" and read out as a single unit, considerably reducing the associated electronic noise.

III. Fluorophores

An advantage of using PME or any time-based detection as opposed to wavelength discriminating detection is the increase in the number of fluorophores, which can be used. At any given excitation wavelength, there are often only about two or three commercially available dyes that emit with narrow enough emission bands with sufficiently separated wavelength maxima that can be individually measured simultaneously (U.S. Pat. No. 6,139,800). If three or more fluorophores can be found, there is still substantial cross-talk or overlap of the emission spectra that will require substantial deconvolution of the spectra with a corresponding increase in the likelihood of error in identifying the species.

One solution to this problem has been the addition of a second laser to allow for the simultaneous or sequential detection of up to approximately six dyes (U.S. Pat. No. 6,139, 800). However, this solution still has the problem of substantial overlap in the spectra and the need for signal intensities great enough to be detected after spectral dispersion of the signal.

Optimally, the way to obtain the highest emission signal possible is to optically match an excitation source with the absorption maxima of a dye with a high molar extinction coefficient. This is done for every fluorophore. However, the excitation source need not match the absorption maxima exactly, instead, it is important to obtain laser-dye combinations where each dye has an absorption maxima which substantially corresponds with one source wavelength with concomitant emission, coupled with minimal absorption/ emission (cross-talk) from the non-matched laser sources used in the assay.

A system with four fluorophores used to detect the 4 DNA bases is preferred. However, 2, 3, 4, 5, 6, 7, 8, 9, 10, 11, 12, 13, 14, 15, or 16 different fluorophores may be used with the PME system.

A non-limiting list of dyes that may be used in the current invention include BODIPY dyes (BODIPY 630/650, BODIPY 650/665, BODIPY 589/616 or BODIPY-TR, BODIPY 581/591 BODIPY 523/547 or BODIPY-R6G, 5,7-dimethyl-BODIPY (503/512) or BODIPY-FL, 1,3,5,7-tetramethyl-BODIPY (495/503), BODIPY-TMR-X or BODIPY (564/570)-X, BODIPY-TR-X or BODIPY (589/616)-X, BODIPY (530/550), BODIPY (564/570), and BODIPY (558/568)), a zanthene dye, a rhodamine dye (rhodamine green, rhodamine red, tetraethylrhodamine, 5-carboxy rhodamine 6G (R6G), 6-carboxy R6G, tetramethylrhodamine (TMR), 5-carboxy TMR or 5-TAMRA, 6-carboxy TMR or 6-TAMRA, rhodamine B, X-rhodamine (ROX), 5-carboxy ROX, 6-carboxy ROX, lissamine rhodamine B, and Texas Red), a fluorescein dye (FITC, 5-carboxy fluorescein, 6-carboxy fluorescein, fluorescein diacetate, naphthofluorescein, HEX, TET, 5-carboxy JOE, 6-carboxy JOE, Oregon Green 488, Oregon Green 500, Oregon Green 514, erythrosin, eosin), a coumarin dye (7-hydroxycoumarin, 7-dimethylaminocoumarin, 7-methoxycoumarin, 7-amino-4-methylcoumarin-3-acetic acid or (AMCA), and Pacific Blue), a cyanine (Cy) dye (Cy3, Cy3.5, Cy5, Cy5.5, Cy7), a phthalocyanine dye, a phycobiliprotein dye, (B-phycoerythrin (B-PE), R-phycoerythrin (R-PE), and allophycocyanin (APC)), a pyrene and a sulfonated pyrene, (cascade blue), a squaraine dye, an Alexa dye (Alexa 350, Alexa 430, Alexa 488, Alexa 532, Alexa 546, Alexa 568, Alexa 594) and Lucifer yellow.

IV. Excitation Sources

A central principle of the PME technology is the discrimination of a mixture of different fluorophores by the time correlation of "colorblind" fluorescence emission triggered by serially pulsing different excitation lasers. This approach significantly contrasts that of the widely used method of wavelength discrimination of fluorescence emission, where a single excitation source, typically an argon ion laser (488 nm and 514.5 nm) excites four spectrally resolvable fluorescent dyes. The dye of this set, which emits at the longest emitting wavelength is usually the least optimally excited, which is due to poor spectral overlap between the excitation source and the dye's absorption maximum. This inefficient excitation has been partially overcome by the use of fluorescence resonance energy transfer (FRET) dye-primers (Ju et al., 1995; Metzker et al, 1996) and dye-terminators (Rosenblum et al., 1997) to increase signal intensities. Obviously, the optimal method in obtaining the highest emission signal possible would be matching the excitation source with the absorption maxima for every fluorophore in DNA sequencing assays.

The invention may use at least one laser and is flexible to accommodate as many different lasers as is feasibly possible. There may be 2, 3, 4, 5, 6, 7, 8, 9, 10, 11, 12, 13, 14, 15, 16, or more lasers, depending on the system.

A single laser may produce 1, 2, 3, 4, 5, 6, 7, 8 or more different wavelengths for the excitation of fluorophores with different absorption maxima. This can be accomplished using the technique of Stimulated Raman Shifting (SRS). This technique may be employed for conversion to either shorter or longer wavelength(s). The Raman effect enables a laser frequency to be modified by discrete increments, (the Stokes and Anti-Stokes shifts). Frequency conversion is accomplished by passing laser light through a suitable crystal or a stainless steel cell containing gas at an elevated pressure, (i.e. several atmospheres). Conversion efficiency for the principal Stokes shift to longer wavelength can be as high as 35%. The nature of the crystal or gas determines the frequency output, for example, $N_2$, $O_2$, $H_2$, $D_2$, and $CH_4$ give shifts of 2330 $cm^{-1}$, 1550 $cm^{-1}$, 4155 $cm^{-1}$, 2987 $cm^{-1}$, and 2917 $cm^{-1}$ respectively, while $Ba(NO_3)_2$ gives a shift of 1047 $cm^{-1}$. A preferred Raman medium for this invention is molecular nitrogen, as 2330 $cm^{-1}$ is about the desired spacing between excitation frequencies.

Until recently, gas lasers have been widely used for the excitation of "blue" and "green" fluorophores with absorption maxima ranging between 488 nm and 543 nm for DNA sequencing applications. In general, these lasers include the argon ion, the krypton ion, and the helium-neon (He—Ne) lasers. These lasers are large in size, highly inefficient and relatively expensive devices. Moreover, the lifetime of gas laser is approximately 1,000-to-3,000 hours of use, which imposes high maintenance cost for these instruments. Despite these disadvantages, the argon ion laser has been widely used in automated DNA sequencing instrumentation for 15 years now (Smith et al., 1986; Probe et al., 1987) and is frequently described as the excitation source in many capillary electrophoresis systems, see below.

On the other hand, semiconductor lasers or laser diodes are much smaller, lighter, and more rugged than any other laser types and have been employed in a wide variety of applications such as CD players, laser printers, and telecommunication systems. These compact lasers typically produce monochromatic light between 630 nm and 1100 nm. These extremely compact, but durable lasers can produce power in the 10-100 mW range and have a useful lifetime of up to 100,000 hours.

The neodymium:YAG (Yttrium Aluminum Garnet) laser is the most common solid-state laser in use today with instruments being found in a variety of applications such as in industry welding of heavy metals, in surgical operating devices, in laboratory spectroscopic equipment, or on unmanned space probes. A solid-state laser is a source in which the active medium is usually a transparent crystal containing a transition metal, (typically 1% or less), such as neodymium, chromium or holmium. Transitions in the metal ion are responsible for the laser's action. These lasers are optically pumped by either broadband flash-lamp sources, or one or more diode laser sources. For blue and green excitation, solid-state lasers contain a frequency doubling or second harmonic generating (SHG) crystal such as lithium borate or potassium titanyl phosphate. For example, the frequency doubled Nd:YAG laser has a fundamental excitation line of 1064 nm, which is doubled by an SHG crystal to generate green 532 nm light.

Until recently, the application of the PME technology has been unrecognized by the lack of available and reliable solid-state lasers that produce monochromatic light at wavelengths between 400 nm and 630 nm. This emerging field, however, has recently produced solid-state lasers that generate monochromatic light at wavelengths of approximately 400 nm, 473 nm, and 488 nm, which becomes suitable for DNA sequencing applications. Thus, the development of PME is uniquely coupled to this emerging field of laser development and well positioned to incorporate new advances in laser technology, when available.

V. Inverse Dispersion

Because of the need for multiple laser beams incident on a single sample, the laser beams must be steered so that they all pass through or contact the sample. This can be accomplished by spatially combining the different laser beams into one overlapping "white" beam.

Other groups have developed devices to combine two or more laser beams. Conemac (U.S. Pat. No. 6,226,126) describes a laser beam mixer having a beam combining element with a transmissive portion and a reflective portion. However, this technology requires that the cross sectional shape of the second, third and so forth laser beams be distorted. Another limitation is that for each laser beam added, the combined beam must pass through an additional optical element, which introduces loss into the system.

U.S. Pat. No. 5,991,082 discloses a lens system that forms narrow superimposable focal lines from multiple focal lines. This system uses a prism with multiple longitudinally arranged facets bounded by parallel ridge lines and can be used to obtain a high energy radiation beam for use in pumping an X-ray laser.

U.S. Pat. No. 6,215,598 discloses an apparatus for concentrating laser beams, which comprises collimating devices that converge the laser beams into a laser beam sheet. A digital optics device shapes and concentrates the laser beam sheet into a narrow overlapping laser beam.

In the present invention, an inverse dispersion system can be used to steer the light from multiple lasers onto a single sample. Inverse dispersion uses optical dispersion elements such as a prism assembly or a diffraction grating positioned such that light from discrete locations is steered to be substantially colinear and/or substantially coaxial upon exiting the system. The term "substantially colinear" means that the laser beams or excitation lines diverge from each other at angles of less than 5°. The term "substantially coaxial" means that the laser beams or excitation lines diverge from each other at angles of less than 5°.

Figure 2:
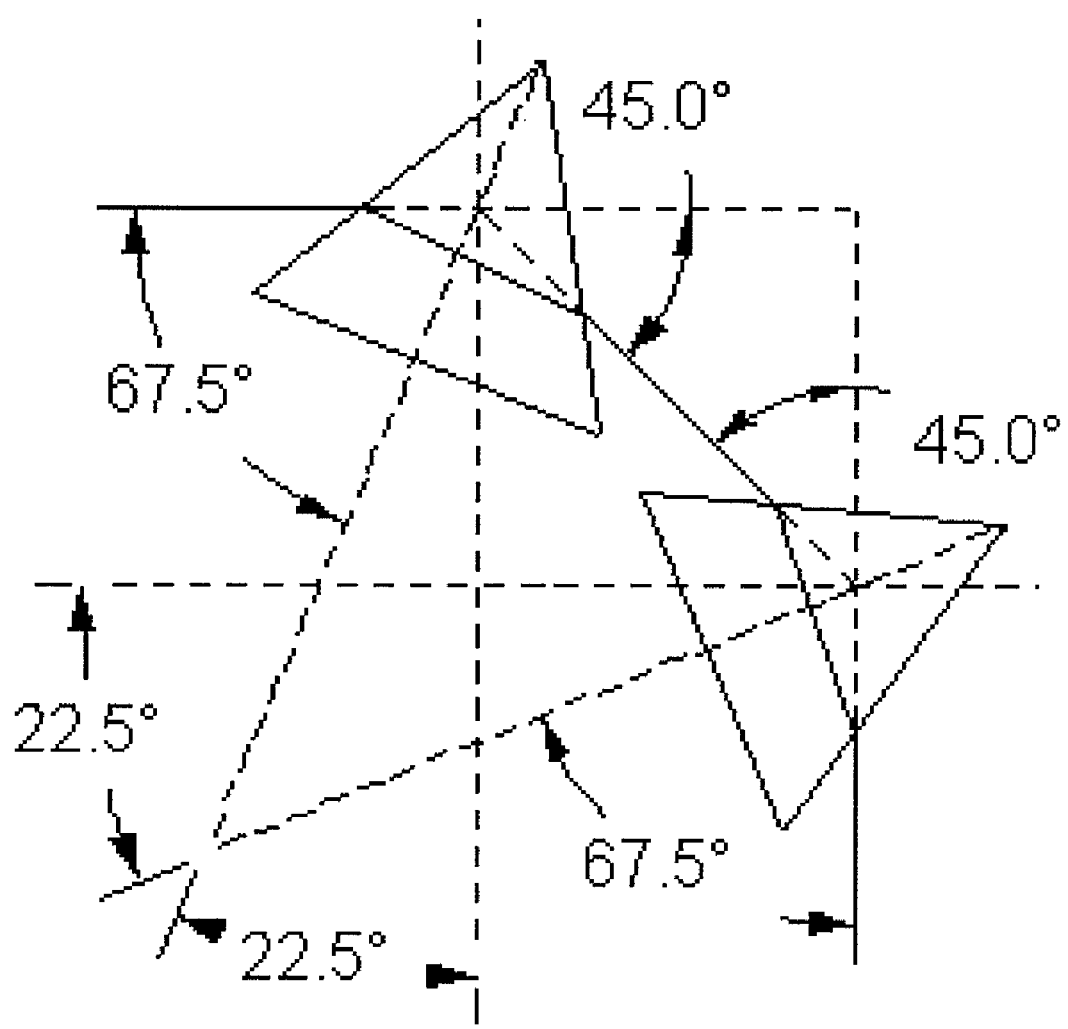
FIG. 2. Inversion dispersion scheme using a dual prism assembly to combine pulsed multiline excitation laser sources from discrete locations. The beams all enter from the left hitting the prism at varying angles and positions on the left side of the first prism (upper left). As they hit the first prism, the laser beams all bend approximately at a 45-degree angle. At this point the beams are not yet colinear and/or coaxial but they are spatially closer together than before. As they hit the second prism, they once again hit at varying angles and positions, and become colinear and/or coaxial as they exit the prism.

The inverse dispersion system may be configured as shown in FIG. 2 in which five excitation lines from discrete locations are combined into a single colinear and/or coaxial line.

High dispersion equilateral prisms constructed from high grade glass, quartz or silica are used in one preferred embodiment of the invention. The preferred orientation for the prisms relative to each other when using high dispersion flint glass prisms is 40°-50°, or more preferred 45°. The preferred orientation for the prisms relative to each other when using quartz prisms is 25°-55° or more preferred 30°-50°. This angle allows efficient overlap of the multiple beams by inverse dispersion into a single beam. A two prism assembly is preferred, however, a single prism or an assembly with three or more prisms is also contemplated. Similarly, a diffraction grating such as a ruled or holographic grating can be used to combine the multiple beams. Multiple excitation lines can be steered onto a diffraction grating such that the diffraction of the grating causes the beams to combine.

In addition to being colinear, the beams may be coaxial, with all of the laser beams passing through the same columnar space in the sample. The same sample molecules will be exposed to each of the laser beams sequentially in turn as the lasers are fired.

The inverse dispersion approach uses the same principle first demonstrated by Sir Isaac Newton, but in reverse direction. In his experiment, collimated white light, from the sun, passed through an equilateral prism, and the various wavelengths became separated by angle. The beam of light passes into the prism, forming a non-zero angle with respect to the normal to the entrance surface. According to Snell's law, all of the rays will be bent towards the normal as the light passes into the more optically dense medium. Due to dispersion of the glass, the shorter wavelengths deviate more. When the rays exit the prism, all are bent a second time, but again, the shorter wavelengths bend more. The result is that the shorter wavelengths now have an angular separation from the longer wavelengths. Blue light is deviated more than green, which is deviated more than yellow, and that in turn more than red.

This process may be reversed, and that is the principle utilized for inverse dispersion. If the separated rays are made to trace paths that are just the reverse of above, then the various wavelengths are combined into a single beam of "white" light. For example, light from lasers, light emitting diodes, arc lamps, incandescent lamps, etc. may be combined (after collimation and spectral filtering, if appropriate) by this inverse dispersion method. The shorter wavelength rays or beams enter the prism at the appropriate larger off-normal angle than the longer wavelength beams. When the correct angles are determined from Snell's law, the beams will all combine into a single coaxial beam. If desired, the beams may be spatially offset to provide colinear beams that, while parallel to each other, pass through the sample at slightly different positions. In the former case, the fluorescence from all of the beams may be imaged onto a single detector. In the latter case, the beams may be imaged onto four or more separate detectors, or separate regions of one detector, such as a CCD camera. If the light sources are pulsed in rapid succession, the combined beam appears to be white or nearly so. If the pulsing is slow enough for the eye to follow, the combined beam will exhibit a changing color pattern originating from the same spatial location.

The prism is typically used at the minimum deviation angle, whereby the entering and exiting angles for a given beam are equal, or as nearly so as practical. The apex bisector will also bisect the angle formed by the entering and exiting beam. If the prism is then rotated, then these two angles are no longer equal. This is advantageous in that it increases both the overall deviation angle and the amount of dispersion. However, this also causes anamorphic changes in the beam diameter. Such anamorphic expansion can be useful if it is desirable to change a round beam cross section to an oblong one, or an oblong beam shape to a round shape. If the inverse dispersion combining of beams is to be done with minimal distortion of the original beam shape, then the minimum deviation angle is preferred.

The angular separation of the beams is increased in proportion to the number of prisms the beam passes through. For example, the use of two identical prisms doubles the angular separation. The anamorphic beam changes can be nearly canceled by using a pair of prisms at non-minimum deviation angles. Use of high dispersion glass, such as flint glass also increases the angular separation of the incoming beams. This in turn reduces the distance needed to achieve spatial separation of the incoming beams, and provides for a more compact optical apparatus. As an example, the present apparatus utilizes two F2 flint glass prisms.

A diffraction grating may also be used as a suitable inverse dispersion element. For a grating exposed to a collimated beam of white light, the beam is diffracted in accordance with the grating equation. If it is a transmission grating, the beam is diffracted away from a straight line path, called the zero order, with the longer wavelengths deviating at a larger angle than the shorter wavelengths. The order of the dispersed wavelengths is the reverse of that for prisms. If a reflection grating is used, again the longer wavelength beam is deviated further from the zero order reflection than a shorter wavelength. As with the prism combiner above, beams of different wavelengths incident on the grating in the reverse direction will provide the same sort of inverse dispersion, leading to a colinearity of the beams. They may be made coaxial if the beams are incident on the same area on the grating but at the appropriate angles for each of the wavelengths. Conventionally ruled gratings are suitable for this purpose, however holographic gratings generally exhibit less scattered light. Gratings generally can be obtained that have considerably higher dispersion than prisms, and hence dispersion angles are larger and the spacing between the light sources can be reduced. They are generally less efficient, so that light losses are greater. Gratings and prisms are both sensitive to the polarization of the light. Since the fluorescence emission is also sensitive to the direction of the polarization, proper orientation of the electric vector of the light should be considered. Polarization rotation devices may be added to improve the transmission efficiency.

VI. Collection Devices

Of the possible choices for detection of fluorescence, the optimum one will depend upon the level of fluorescence intensity. For all detectors described herein, a photon striking the detector is converted into a charge carrier, which is then detected electronically. Charge carriers, however, are generated by extrinsic processes unrelated to the fluorescence signal from a variety of sources: thermal generation, cosmic rays, and natural radioactivity. All carriers generated both from fluorescence and from unrelated sources contribute to shot noise, a well-understood statistical phenomenon. Of the extrinsic sources of excess carrier noise, thermal generation of carriers is usually the dominant extrinsic noise source, which can be reduced by cooling the detector. Fundamentally all that is needed for satisfactory detection is that the number of charge carriers generated by fluorescence during an observation time window is much greater than the square root of the number of all carriers generated during the same time interval. However, once the carriers leave the detector, the amplifying electronics will introduce noise as well, and this electronic noise may dominate. To avoid this situation, devices have been invented that incorporate their own very low noise amplifiers. There are two such devices: the photomultiplier tube (PMT) and the silicon avalanche photodiode (APD). Another approach to reducing amplifier noise is to collect carriers for a period of time and then rapidly read the collected charges out. This mode of operation is used for photodiode array charge-coupled device (CCD) detectors.

For light levels with high enough signals that the noise generated in the external amplifiers is negligible, the simplest device for fluorescence detection is the silicon PIN detector. This device consists of a thin hole rich region (p) and an electron rich region (n) separated by thick carrier deficient region (i). It is back-biased with a negative voltage applied to the p side and a positive voltage applied to the n side. Light striking it penetrates the p region and is absorbed in the i region generating an electron hole pair with the electron being attracted to the n side and the hole to the p side creating a current through the device. The quantum efficiency of this process is very high (~80%). Because it is the simplest, most compact, and cheapest detector, the silicon PIN is a preferred detector. Other, more sensitive detectors may also be used for detecting low levels of light emission for a multi-capillary electrophoresis system and direct detection assays.

The silicon PIN detector can be made suitable for the detection of very low light levels by introducing carrier gain into it. A photon strikes the detector creating an electron hole pair. The electron is accelerated by an electric field and creates additional carriers by ionization. The additional electrons are accelerated to produce more carriers resulting in an avalanche process and current gain. Silicon avalanche detectors operate in two modes analogous to that of the PMT: an analog current measurement mode and a digital counting mode. When operated in the analog mode, the current gain (~300) is less than that of a PMT ($\sim 10^5$-$10^6$), but with exception to the lowest light levels, the signal is still much larger than the noise in the external amplification circuit. In addition, the wavelength response range (300 to 1100 nm) of silicon detectors is much wider than any individual PMT photocathode, covering the fluorescent maximum of any dye that might be used for DNA sequencing instrumentation.

Alternatively, a silicon APD can be thermoelectrically cooled and operated in the Geiger counting mode, where individual fluorescence photons are counted. This provides a high quantum efficiency (~80%) with dark count levels approaching a cooled PMT (quantum efficiency typically 10%). The thermoelectrically cooled silicon APD provides a compact form combined with state-of-the-art sensitivity. While higher sensitivity may not be required for detecting fluorescent signals from standard sequencing reactions, silicon APDs in the counting mode can be ideal for detecting fluorescent signals directly from genomic DNA assays (i.e., without amplification).

Detectors with the required characteristics are commercially available and include the simple silicon PIN detector, the silicon APD, or a photodiode array (CCD). The simple silicon detector is the cheapest, the silicon avalanche is the most sensitive, and the CCD is most useful for multiple capillary systems as it provides many detectors in a single unit.

VII. Coupled Systems

The PME technology has sufficient flexibility for coupling to a variety of formats, for example, the PME system can be coupled to conventional capillary electrophoresis (CE) or to separation and/or purification using high-density arrays/biochips. Ideally, a DNA sequencing system capable of direct detection of fluorescent assays for genomic DNA should (i) optimally excite all fluorescent dyes, (ii) be capable of efficiently collecting photons over a large part of the UV, visible and infrared spectrum, (iii) continuous monitoring of fluorescent signals in high-throughput array or high-density formats, (iv) maximize fluorescence emission signals for detection, (v) be configured to minimize background scattered light, and be automated using replaceable gel matrices.

a. Capillary Electrophoresis

The PME fluorescence detection system of the present invention can be coupled to conventional capillary electrophoresis (CE) as a preferred method for resolving DNA fragments.

Microcapillary array electrophoresis generally involves the use of a thin capillary or channel, which may or may not be filled with a particular separation medium. Electrophoresis of a sample through the capillary provides a size-based separation profile for the sample. The use of microcapillary electrophoresis in size separation of nucleic acids has been reported in, e.g., Woolley and Mathies (1994). The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Microfabrication of microfluidic devices including microcapillary electrophoretic devices has been discussed previously (e.g., Jacobsen et al., 1994; Effenhauser et al., 1994; Harrison et al., 1993; Effenhauser et al., 1993; Manz et al., 1992; and U.S. Pat. No. 5,904,824). Typically, these methods comprise photolithographic etching of micron scale channels on a silica, silicon or other crystalline substrate or chip, and can be readily adapted for use in the present invention. In some embodiments, the capillary arrays may be fabricated from the same polymeric materials described for the fabrication of the body of the device, using the injection molding techniques described herein.

Tsuda et al., (1990), describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art, which may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acids in the sample.

The use of replaceable gel matrices, which suppress electroendoosmotic flow and DNA-capillary wall interactions such as polydimethylacrylamide (Madabhushi, 1998), may be used for electrophoretic separations in the present invention.

b. Chromatographic Techniques

Alternatively, chromatographic techniques may be coupled to the PME fluorescence detection system of the present invention. There are many kinds of chromatography, which may be used including liquid chromatography, HPLC and many specialized techniques, such as reverse phase HPLC, normal phase HPLC, anion exchange, cation exchange, denaturing HPLC, size exclusion or gel permeation, and hydrophobic interaction.

c. Microfluidic Techniques

Microfluidic techniques can be used for fluid flow with the PME system, and includes the use of a platform such as microcapillaries, designed by ACLARA BioSciences Inc., or the LabChip™ "liquid integrated circuits" made by Caliper Technologies Inc. Miniaturizing some of the processes involved in genetic analysis has been achieved using microfluidic devices. For example, published PCT Application No. WO 94/05414, by Northrup and White, incorporated herein by reference, reports an integrated micro-PCR™ apparatus for collection and amplification of nucleic acids from a specimen. U.S. Pat. No. 5,304,487 to Wilding et al., and U.S. Pat. No. 5,296,375 to Kricka et al, discuss devices for collection of cell containing samples and are incorporated herein by reference. U.S. Pat. No. 5,856,174 describes an apparatus, which combines the various processing and analytical operations involved in nucleic acid analysis and is incorporated herein by reference.

d. Chip Technologies

Specifically contemplated by the present inventors for combining with the PME system are chip-based DNA technologies. These techniques involve quantitative methods for analyzing large numbers of genes rapidly and accurately.

Chip based technologies that can be used in the current invention include the those described in U.S. Pat. No. 6,153,379 and Shumaker et al. (1996) where a method of analyzing oligonucleotides is described in which oligonucleotides are extended with fluorescent dideoxynucleotides, and detected using an automated fluorescent DNA sequencer. The oligonucleotide length identifies the known mutation site, and the fluorescence emission of the ddNTP identifies the mutation. Another method of analyzing oligonucleotides involves using template DNA annealed to an oligonucleotide array. The analysis is done using a Phosphor Imager and alpha-$^{32}$P labels. Kurg et al., (2000) describes an integrated system with DNA chip and template preparation, multiplex primer extension on the array, fluorescence imaging, and data analysis. The method includes annealing DNA to immobilized primers, which promote sites for template-dependent DNA polymerase extension reactions using four unique fluorescently labeled dideoxy nucleotides. A mutation is detected by a change in the color code of the primer sites.

Motorola BioChip Systems has the I-based SNP systems with array technology centered on a three-dimensional gel pad format consisting of flexible content architectures.

The MassARRAY system, developed by SEQUENOM (U.S. Pat. Nos. 5,547,835, 6,238,871, and 6,235,478) has a platform capable of high throughput SNP analysis using enzymology, bioinformatics and miniaturized chip-based disposables with mass spectrometry detection. The MassARRAY technology can be used to distinguish genotypes using MALDI-TOF mass spectrometry. DNA fragments associated with genetic variants are simultaneously separated and detected, measuring target DNA associated with SNPs and other forms of genetic variation directly.

f. Bead Technologies

The PME system may be coupled with microbeads containing bound DNA or RNA segments. These beads may be plain or coated with material such as biotin, terminal amines, or Protein G to facilitate binding of the biomolecule to the bead. Microbeads may be used in conjunction with, for example, microfluidic systems or electrophoretic systems and PME detection. The beads may be porous or solid and made of polymers such as polystyrene or agarose and may optionally contain magnetic particles, such as those obtained from Dynal thus allowing use in magnetic separation techniques. The beads may also be porous thereby providing increased surface area for binding. Magnetic beads are used in a manner similar to polymer beads. However, these beads contain a magnetic source such as $Fe_2O_3$ or $Fe_3O_2$ that can be used for rapid and simple separation.

VIII. Continuous Fluorescence Monitoring

To capture minute fluorescent signals for multiple capillary array or other formats derived from direct assays, the high duty cycle of continuous monitoring systems has significant advantage over scanning systems. Moreover, continuous systems have other benefits that simplify the mechanical operation of the system, such as no moving mechanical stages that wear down, break down, or become misaligned. These systems use the laser light power more efficiently allowing greater operation of fluorescence excitation under photobleaching conditions. Basically, there are two known methods for continuous monitoring of fluorescent signals, namely on-column and post-column detection. Both methods can be used with the PME technology of the current invention for DNA sequencing applications using capillary electrophoresis.

a. On-Column Detection

The first on-column detection schemes were described using single capillary systems (Luckey et al., 1990; Swerdlow et al., 1990; Drossman et al., 1990; Cohen et al., 1990). In 1990, the Smith group described the first 4-color on-column system using a multi-line argon-ion laser (488 nm and 514.5 nm) to illuminate a single capillary. The fluorescence emitted from FAM, JOE, TAMRA, and ROX dye-labeled sequencing reactions was collected orthogonal to the excitation source and using a set of beamsplitters, the emitted fluorescence was directed to a set of 4 PMT detectors (Luckey et al., 1990). Karger et al. described the first on-column, spectral dispersion system using a CCD camera (Sweedler et al., 1991) to detect emission wavelengths approximately in the range of 500 nm to 650 nm derived from the fluorescence of a 4-color sequencing reaction. Similar to the Smith design, the fluorescence was collected perpendicular to the excitation path, but the authors describe the unique feature of 4 target areas that correspond to the emission properties of FAM, JOE, TAMRA, and ROX dye-labeled reactions and the binning of pixels within the target areas for enhanced readout speed and reduced readout noise (Karger et al., 1991).

The first capillary array instrument was a modified DuPont GENESIS 2000 DNA sequencing instrument (Probe et al., 1987), which the slab gel was replaced with a 12-capillary array (Zagursky et al., 1990). An argon-ion laser beam (single line 488 nm) was scanned across the capillaries and fluorescence was detected using the 510 nm and 540 nm resolved, two PMT detector scheme. The Mathies group has described a confocal-fluorescence system, which has potential for improved signal to noise and scanned back and forth using a motor-driven translation stage across a 24-capillary array (Huang et al., 1992). Fluorescence was collected using a 180° geometry to the argon ion laser (488 nm) excitation source by confocal detection. Originally, a two PMT detector system coupled to a two-dye binary coding method was used with different mole fraction combinations of FAM and JOE dye reactions to differentiate the four-termination reaction set (Huang et al., 1992). Recently, the Mathies group developed a 4-color confocal scanning detection system that directs the fluorescence emission through a number of different dichroic beamsplitters to 4 PMT detectors (Kheterpal et al., 1996). The 4-color confocal scanning system described here represents the core technology for the commercially available 96-capillary MegaBACE 1000 instrument (Molecular Dynamics). More recently, the Riken group has described a 384-capillary DNA sequencer, which uses an argon ion laser in a scanning mode and splits the fluorescence emission signal to 4 different band-pass filters coupled to dedicated PMT detectors (Shibata et al., 2000). Although mechanical scanning systems can uniformly illuminate each capillary in the array, in general, they can be problematic due to breakdown and misalignment, low duty cycle, and potential photobleaching by duty cycle compensation with higher laser power levels.

Several side-entry illumination schemes directly through capillary arrays have been problematic in scaling from a single capillary to array systems, mainly because of reflection and refraction of the laser beam at the capillary boundaries. The Yeung group described a 10-capillary system that used axial beam illumination and CCD detection, in which individual optical fibers coupled via an argon ion laser were directly inserted into the ends of the capillary tubes (Taylor et al., 1993). The intrusion of optical fibers into separate capillaries, however, affected the electroendoosmotic flow and increased the possibility for contamination and clogging (Lu et al., 1995). This group also described illumination by a line of laser light focused across the array using a plano-convex cylindrical lens to illuminate a 100-capillary array (Ueno et al., 1994); however, this design inefficiently used less than 0.5% of the laser power to illuminate each capillary (Lu et al., 1995). Quesada and Zhang (1996) described an 8-capillary prototype in which argon ion illumination and fluorescence detection were achieved by using individual optical fibers constructed in an orthogonal geometry and imaged through a spectrograph using a CCD camera. Scaling beyond the initial individual optical fiber design, however, was reported to be problematic because of the increased demand on laser power, and the bulkiness and irregular alignment of the optical junction connectors to each capillary tube (Quesada et al., 1998).

To address the loss of laser illumination by refraction, two independent groups have demonstrated that refracted laser light at the capillary surface can be focused repeatedly under optimized optical conditions and produce a waveguiding effect (Quesada et al., 1998; Anazawa et al., 1996). Quesada et al. (1998) demonstrated that a bi-directionally illuminated waveguide system using an argon ion laser showed good illumination across a 12-capillary array with a difference of less than 10% across the array, and with potential for scaling to a 96-capillary system with near uniform illumination. Alternatively, index matching of the capillary array has also been shown to reduce laser light refraction and scattering across the array (Lu et al., 1995), but to a smaller degree than waveguide illumination (Quesada et al., 1998).

b. Post-Column Detection

The first post-column detection schemes also described single capillary systems (Swerdlow et al., 1990; Swerdlow et al., 1991). The Dovichi group first reported a 4-color post-column detection system using a sheath flow cuvette (Swerdlow et al., 1990). These authors demonstrated the sheath flow concept using the four-spectral channel system based on the work described by the Smith group (Luckey et al., 1990) and a two-spectral channel system based on the work described by Prober et al. (1987). Unlike the beamsplitter design, the four-spectral channels were discriminated using a rotating wheel containing 4 specific band-pass filters, which was synchronized to a sector wheel that alternated the excitation source between an argon-ion laser (488 nm) and a green He—Ne laser (543.5 nm). The appropriate orientation of the filter wheel directed the specific emission light wavelengths of FAM, JOE, TAMRA, and ROX dye-labeled sequencing reactions to a single PMT detector. The two-spectral channel, two intensity system used a single argon-ion laser (488 nm) to excite the 4-different succinyl-fluorescein dye-labeled reactions, which have limited spectral resolution. The emission fluorescence centered at 510 nm and 540 nm was uniquely split using a single dichroic mirror and detected with two PMT detectors. The assignment of the nucleotide sequence was performed by determining the ratio of baseline-corrected peak intensities (Prober et al., 1987).

The post-column sheath-flow approach has the advantage of eliminating excitation light scattering at the capillary surfaces and in illuminating all capillary tracks simultaneously. Kambara and Takahashi described the first multiple sheath-flow capillary array system using a He–Ne laser (594 nm) and single color Texas Red (ROX) labeled DNA sequencing reactions (Kambara et al., 1993). This system was later developed into a 4-color system using the combined excitation lines from both an argon ion laser (488 nm) and a YAG laser (532 nm) to simultaneously irradiate FAM, JOE, TAMRA, and ROX dye-labeled reactions. The fluorescence was dispersed using an image-splitting prism, passed through 4 different optical filters, and detected as two-dimensional line images using a cooled CCD camera (Takahashi et al., 1994). The Hitachi technology described here represents the core technology for the commercially available 96-capillary 3700 DNA sequencer instrument (Applied Biosystems).

Another application of the sheath flow approach to post-column detection was described in U.S. Pat. No. 6,139,800 where fluorescent detection of labeled particles is accomplished for capillary electrophoresis. Multiple wavelength sources excite the labeled particles and multiple wavelength discriminating detectors detect the sample emissions.

Capillary array sheath-flow cuvettes require careful attention to hydrodynamic focusing, which can be achieved by uniformly spacing the capillaries in the cuvette holder. Recently, the Dovichi group has described two sheath flow cuvettes, the rectangular cuvette that is tapered to force 5-capillaries to squeeze together (Zhang et al., 1999) and the micromachined cuvette with uniformly spaced etched grooves to align 16 individual capillaries (Crabtree et al., 2000). Of the two designs, the latter one shows more promise for scaling to a 96-capillary array.

IX. Obtaining High Sensitivity and Low Background Scattered Light

In 1990, several groups reported limit of detection values corresponding to $10^{-19}$ moles for CE systems and were performed using a $10^{-11}$ M solution of fluorescein flowing continuously in an open capillary (Swerdlow et al., 1990; Drossman et al., 1990). These systems, however, were roughly 10-fold less sensitive than the sheath flow detector system, which has a reported detection limit of $10^{-20}$ moles (Swerdlow et al., 1990; Kambara et al., 1993). Coupled to an APD operating in the Geiger counting mode, this sheath flow system described recently by the Dovichi group showed a limit of detection of 130±30 fluorescein molecules (Zhang et al., 1999).

The number of fluorescence counts generated is the product of two factors: (i) the number of fluorescence photons generated and (ii) the overall counting efficiency. The number of fluorescence photons generated is given by $$Np = \frac{\sigma NP}{Ahv} QYt$$

where N is the number of dye molecules being excited, P is the laser power (J/s), σ is the absorption cross-section (cm²), A is the area of the laser beam, hv is the energy of an excitation photon (J), QY is the quantum yield for fluorescence, and t is the observation time (s). The overall counting efficiency is given by $$Eff = \frac{SA \cdot QE}{4\pi}$$

where SA is the solid angle of fluorescent light collection (in steradians) and QE is the quantum efficiency of the detector. Assuming that the cross-section is $3.8 \times 10^{-16}$ cm² (ε=100,000 liters/(mol-cm)), the wavelength of the excitation is 600 nm, the QY is unity, the numerical aperture is unity, and the quantum efficiency is 0.8, then $$Np = 73\frac{NPt}{A}$$

The PME system of the current invention is useful as a DNA sequencing device for analyzing SNPs directly from genomic DNA without cloning or PCR amplification. Estimating 106 white blood cells per cm$^3$ of blood, one calculates 73,000 counts in a second could be expected for a single SNP probing of 1 ml of blood without any concentration of solution with a laser power of 1 mW and an area of 1 cm$^2$. Concentration would reduce A without reducing N. Thus, there is an easily detectable signal without electrophoresis or heroic measures, granted that the sequencing assays are free of unincorporated dye. Note that focusing the laser reduces N, but simultaneously reduces A by the same factor so that the signal does not depend upon focusing as long as the numerical aperture can be maintained (defocusing limit) or the dye is not destroyed by two photon absorption effects (tight focusing limit).

The situation is somewhat different when determining a number of SNPs simultaneously. Then electrophoresis becomes necessary in order to separate the various fragments. Typically in Sanger sequencing, a 10-to-30 μL sample is introduced into the 3700 DNA sequencing instrument, but only about 10 nL is actually introduced into the capillary. This is a loss in N of about a factor of 1000-to-3000 reducing N to ~100-to-300. However, if using the sheath flow approach (Anazawa et al., 1996; Zhang et al., 1999), the dye-tagged fragments emerging from a 50 μm ID capillary will occupy a cylinder about 2 mm long and perhaps 100 μm in diameter. Its cross-sectional area A will be 2×10$^{-3}$ cm$^2$ and the number of counts in a 1 s counting interval will be $$Np = 73\frac{300 \cdot 0.001 \cdot 1}{0.002} = 11,000$$

This calculation is consistent with the report by Zhang et al. (1999) that 130 fluorescein molecules emerging from a 50 μm capillary could be detected in 0.2 sec counting time. It will be possible to reduce the wastage factor of 3000 cited above to perhaps 100 by devising low volume methodologies to use a 1 μL sample.

Thus, a capillary electrophoresis system that utilizes multiple, compact solid-state lasers and laser diodes coupled to highly efficient detection devices, which employ continuous illumination and sheath flow detection features is a preferred embodiment of the current invention. These integrated technologies are well suited for the application of the PME technology and have sufficient feasibility for direct detection assays.

X. Single Nucleotide Polymorphisms (SNPs)

Spontaneous mutations that arise during the course of evolution in the genomes of organisms are often not immediately transmitted throughout all of the members of the species, thereby creating polymorphic alleles that co-exist in the species populations. Often polymorphisms are the cause of genetic diseases. Several classes of polymorphisms have been identified. For example, variable nucleotide tandem repeats (VNTRs) are polymorphic and arise from spontaneous tandem duplications of di- or trinucleotide repeated motifs of nucleotides. If such variations alter the lengths of DNA fragments generated by restriction endonuclease cleavage, the variations are referred to as restriction fragment length polymorphisms (RFLPs). RFLPs are been widely used in human and animal genetic analyses and forensic and paternity testing.

Another class of polymorphisms is generated by the replacement of a single nucleotide. Such single nucleotide polymorphisms (SNPs) rarely result in changes in a restriction endonuclease site. SNPs are the most common genetic variations and occur once every 300-to-1000 bases, and several SNP mutations have been found that affect a single nucleotide in a protein-encoding gene in a manner sufficient to actually cause a genetic disease. SNP diseases are exemplified by hemophilia, sickle-cell anemia, hereditary hemochromatosis, late-onset Alzheimer disease, etc.

SNPs can be the result of deletions, point mutations and insertions and in general any single base alteration, whatever the cause, can result in a SNP. The greater frequency of SNPs means that they can be more readily identified than the other classes of polymorphisms. The greater uniformity of their distribution permits the identification of SNPs "nearer" to a particular trait of interest. The combined effect of these two attributes makes SNPs extremely valuable. For example, if a particular trait reflects a mutation at a particular locus, then any polymorphism that is linked to the particular locus can be used to predict the probability that an individual will be exhibit that trait.

Several methods have been developed which can be combined with PME technology to screen polymorphisms and some non-limiting examples are listed below. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism, or any other biochemical interpretation.

a. DNA Sequencing

Traditionally, DNA sequencing has been accomplished by the "dideoxy-mediated chain termination method," also known as the "Sanger Method" (Sanger, F., et al., 1975), which involves the chain termination of DNA synthesis by the incorporation of 2',3'-dideoxynucleotides (ddNTPs) using DNA polymerase. The reaction also includes the natural 2'-deoxynucleotides (dNTPs), which extend the DNA chain by DNA synthesis. Thus, balanced appropriately, competition between chain extension and chain termination results in the generation of a set of nested DNA fragments, which are uniformly distributed over thousands of bases and differ in size as base pair increments. Electrophoresis is used to resolve the nested set of DNA fragments by their respective size. The fragments are then detected by the previous attachment of four different fluorophores to the four bases of DNA (i.e., A, C, G, and T), which fluoresce at their respective emission wavelengths after excitation at their respective excitation wavelengths using PME technology. The DNA sequencer may be based on an electrophoresis system with the throughput capacity of a single column, 4, 8, 16, 48, 96 or 384-capillary instrument or may integrate with other separation platforms, including high-density chip arrays.

Similar methods which can be used with PME technology include the "chemical degradation method," also known as the "Maxam-Gilbert method" (Maxam, A. M., et al., 1977). Sequencing in combination with genomic sequence-specific amplification technologies, such as the polymerase chain reaction may be utilized to facilitate the recovery of the desired genes (Mullis, K. et al., 1986; European Patent Appln. 50,424; European Patent Appln. 84,796, European Patent Application 258,017, European Patent Appln. 237,362; European Patent Appln. 201,184; U.S. Pat. No. 4,683,202; U.S. Pat. No. 4,582,788; and U.S. Pat. No. 4,683,194).

b. Primer Extensions Methods for SNP Detection

A preferred assay for the detection of multiple SNPs is the single nucleotide primer extension method, which has also been called single nucleotide incorporation assay and primer-guided nucleotide incorporation assay. These methods rely on the specific hybridization of an identically complementary oligonucleotide sequence to the genetic region or target of interest, which has been amplified by the polymerase chain reaction (PCR) or cloned using standard molecular biology techniques (Sambrook et al., 1989). However, unlike the Sanger reaction, the primer extension method is assayed using either single unlabeled or labeled dNTPs, 3'-modified-dNTPs, base-modified-dNTPs, or alpha-thio-dNTPs or a mixture of ddNTPs, which all can chain terminate DNA synthesis under appropriate conditions following the incorporation of a single nucleotide (U.S. Pat. Nos. 4,656,127; 5,846,710; 5,888,819; 6,004,744; 6,013,431; 6,153,379, herein incorporated by references). Here, the word usage of 2'-deoxynucleoside triphosphate, 2'-deoxyribonucleoside triphosphate, dNTP, 2'-deoxynucleotide, 2'-deoxyribonucleotide, nucleotide or natural nucleotide are used as synonymous terms and used interchangeably in the current patent document.

1. Using Single Unlabeled dNTPs

A method, called pyrosequencing, uses singly added unlabeled dNTPs and is based on a repetitive cyclic method of start-stop DNA synthesis of single nucleotide addition. Pyrosequencing is a mini-sequencing technique and relies on a multi-enzyme cascade to generate light by luciferase as the mode of detection (Nyren et al., 1993; Ronaghi et al., 1998). PCR amplified DNA fragments, which contain a 5'-biotin group are immobilized on streptavidin-coated magnetic beads. An incorporated unlabeled nucleotide event is monitored by the release of inorganic pyrophosphate and the subsequent release of light following the primer extension step. Because pyrosequencing is a cyclic DNA sequencing strategy, the placement of the oligonucleotide immediately adjacent to the 5'-position is not always required, and the primer can be placed within the sequencing read-length of the method, usually 20 bases. Major disadvantages with the pyrosequencing technique are the method has low sensitivity, the high cost of the reagents, particularly the enzymes, and sequence difficulties with homopolymer repeats (i.e., AAAAA) and high "GC" rich regions.

2. Using Single Labeled dNTPs

Unlike the pyrosequencing method, which can extend the primer beyond a single nucleotide position, other investigators have reported single nucleotide incorporation assays using single nucleotides labeled with radioactive, non-radioactive, or fluorescent tags (Sokolov, 1990; Syvanen et al., 1990; Kuppuswamy et al., 1991; Prezant and Ghodsian, 1992). In these strategies, the placement of the oligonucleotide is immediately adjacent to the 5'-position of the single nucleotide mutation site under investigation. Sokolov showed the specific incorporation and correct identification of single nucleotide sequences of a known sequence in the cystic fibrosis gene using alpha $^{32}$P-dCTP and alpha $^{32}$P-dGTP (Sokolov, 1990). In another report, a similar approach was described for the detection of the Δ508 mutation in the cystic fibrosis gene and point mutations in exon 8 of the factor IX gene (Hemophilia B) (Kuppuswamy et al., 1991). Following PCR amplification of specific target regions, specific oligonucleotides, which hybridized immediately adjacent to the 5'-position of the mutation under investigation, were extended by one nucleotide using single alpha $^{32}$P-dNTPs. Moreover, a dual labeling strategy for SNP detection was reported for exon 4 of the apolipoprotein E gene using different combinations of $^{3}$H-labeled dTTP, alpha $^{32}$P-labeled dCTP, or digoxigenin-11-dUTP. Following immobilization of PCR-amplified fragments on avidin-coated polystyrene beads, single nucleotide extension assays were performed and incorporated nucleotides were detected using a liquid scintillation counter at different window settings for $^{3}$H and $^{32}$P radioactivity or colorimetrically using an alkaline phosphatase assay (Syvanen et al., 1990). A similar method, called Trapped-Oligonucleotide Nucleotide Incorporation (TONI) using a biotinylated primer immobilized on streptavidin magnetic beads and singly added alpha $^{32}$P-labeled dNTPs was described for genetic screening of mitochondrial polymorphisms and different hemoglobin genotypes (Prezant and Ghodsian, 1992).

3. Using Single 3'-Modified dNTPs

Metzker et al. proposed the base addition sequencing strategy (BASS), which is a mini-sequencing technique and involves stepwise single nucleotide sequencing by repetitive cycles of incorporation of 3'-O-modified nucleotides, detection of the incorporated nucleotide, and deprotection of the 3'-O-modified nucleotide to generate the 3'-OH substrate and allow for the next cycle of DNA synthesis (Metzker et al., 1994). Eight different 3'-O-modified dNTPs were synthesized and tested for incorporation activity by a variety of DNA polymerases. 3'-O-(2-Nitrobenzyl)-dATP is a UV sensitive nucleotide and was shown to be incorporated by several thermostable DNA polymerases. Base specific termination and efficient photolytic removal of the 3'-protecting group was demonstrated. Following deprotection, DNA synthesis was reinitiated by the incorporation of natural nucleotides into DNA. The identification of this labile terminator and the demonstration of a one-cycle stop-start DNA synthesis identified the initial steps in the development of a novel sequencing strategy. The major challenge for SNP detection using BASS, however, is the continued synthesis and identification of novel 3'-modified nucleotides that give the desired properties of termination with removable protecting groups.

4. Using Single Base-Modified 3'-dNTPs

Kornher and Livak (1989) described another method by incorporating mobility shifting modified-dNTPs (i.e., the attachment of a biotin group or a fluorescein group to the base) into a PCR amplified DNA sample. The SNP is identified by denaturing gel electrophoresis by observing a "slower" migrating band, which corresponds to the incorporated modified nucleotide into the DNA fragment.

5. Using Single alpha-thio-dNTPs

Other methods that can be employed to determine the identity of a nucleotide present at a polymorphic site utilize modified alpha-thio-dNTPs, which are resistant to exonuclease cleavage (U.S. Pat. No. 4,656,127). An oligonucleotide, of identical sequence to a complementary target region, immediately flanks the 5'-position of the single nucleotide mutation site under investigation. If the polymorphic site on the DNA contains a nucleotide that is complementary to the particular exonuclease-resistant nucleotide derivative present, then that derivative will be incorporated by a polymerase and extend the oligonucleotide by one base. Such incorporation makes the primer resistant to exonuclease cleavage and thereby permits its detection. As the identity of the exonuclease-resistant nucleotide derivative is known one can determine the specific nucleotide present in the polymorphic site of the DNA.

6. Using Single Labeled 2',3'-dideoxynucleotides

Several groups have reported methods for single nucleotide incorporation assays using labeled 2',3'-dideoxynucleotides to specifically assay given SNPs of interest, which are detected by autoradiography, calorimetrically, or fluorescently (Lee and Anvret, 1991; Livak and Hainer, 1994; Nikiforov et al., 1994; Shumaker et al., 1996). All of these methods rely on PCR to amplify genomic DNA from patient material and careful design of oligonucleotide sequences to target specific known mutations in different genes. The separation of dideoxynucleotide incorporated DNA fragments can be achieved electrophoretically (Lee and Anvret, 1991; Livak and Hainer, 1994; Nikiforov et al., 1994; Shumaker et al., 1996) or by using high-density array chip formats (Shumaker et al., 1996).

7. By Direct Detection from Genomic DNA

One aspect of this invention is to develop a DNA sequencing device for analyzing SNPs directly from genomic DNA without cloning or PCR amplification. The present invention circumvents the problems associated with the previously described methods for SNP detection, which rely on a prior PCR or cloning step. These steps potentially add errors in sample handling, introduction of exogenous contamination, significant costs in reagents and labor and seriously hamper the introduction of high-throughput SNP detection into a clinical or medical setting. Because of its simplicity, the PME technology has the capability of greatly increasing the multiplexing of numerous SNPs simultaneously, which is significantly limited in other previously described systems. For example, 4-, 8-, 12- and 16-different fluorophores identified herein can be coupled to appropriate ribonucleotides, 2'-deoxynucleotides, 2',3'-dideoxynucleotides, 2'3'-unsaturated-dNTPs and/or other modified nucleotides.

Moreover, the assay can be multiplexed, and coupled to a high-throughput electrophoresis system, and in this configuration, it has the capability of analyzing 2,000-to-4,000 independent SNPs in approximately 30-to-60 minutes. Multiplexing is accomplished by varying the length of the specific primers by increments of 2-to-3 bases, and by increasing the number of fluorophores detected in the SNP assay. Twenty to 100, or more specifically 30-to-50 primers, all differing in length, could be assayed in a single nucleotide primer extension assay, which could be resolved by electrophoresis and detected by PME in a single capillary. Since the longest primer sequence will generally not exceed 100 bases in length, fast separation times are expected. It is noteworthy that SNP specific primers can also be arrayed in a high-density chip format, thus eliminating the need for electrophoresis. The scalability of the DNA sequencer is multiplied by 96-capillaries.

c. Massively Parallel Signature Sequencing (MPSS) Strategy

Brenner et al. (2000) recently presented data on their massively parallel signature sequencing (MPSS) strategy, which is another cyclic process involving type II restriction digestion/ligation/hybridization to sequence over 269,000 signatures of 16-20 bases in length (Brenner et al., 2000). The main disadvantage of MPSS is low efficiency where only 25% of the starting DNA templates yield signatures after application of the base-calling algorithms.

d. Ligase Chain Reaction (LCR)

LCR can also amplify short DNA regions of interest by iterative cycles of denaturation and annealing/ligation steps (Barany, 1991). LCR utilizes four primers, two adjacent ones that specifically hybridize to one strand of target DNA and a complementary set of adjacent primers that hybridize to the opposite strand. LCR primers must contain a 5'-end phosphate group such that thermostable ligase (Barany, 1991) can join the 3'-end hydroxyl group of the upstream primer to the 5'-end phosphate group of the downstream primer. Successful ligations of adjacent primers can subsequently act as the LCR template resulting in an exponential amplification of the target region. LCR is well suited for the detection of SNPs since a single-nucleotide mismatch at the 3'-end of the upstream primer will not ligate and amplify, thus discriminating it from the correct base. Any or all of the LCR primers can be labeled with different fluorescent dyes for unambiguous discrimination of specific SNPs. Although LCR is generally not quantitative, linear amplifications using one set of adjacent primers, called the Ligase Detection Reaction, can be quantitative. Coupled to PCR, linear ligation assays can also be used as a mutation detection system for the identification of SNPs using both wild-type-specific and mutant-specific primers in separate reactions.

e. Oligonucleotide Ligation Assay (OLA)

The Oligonucleotide Ligation Assay was first reported to detect SNPs from both cloned and clinical materials using a 5'-end biotin group attached to the upstream primer and a nonisotopic label attached to the downstream primer (Landegren et al., 1988). Allele-specific hybridizations and ligations can be separated by immobilization to a streptavidin-coated solid support and directly imaged under appropriate conditions without the need for gel electrophoretic analysis. Subsequently, Nickerson et al. have described an automated PCR/OLA method for the diagnosis of several common genetic diseases. Following PCR amplification, the upstream 5'-end biotinylated primer and digoxigenin labeled downstream primer are ligated together under appropriate and specific annealing conditions, captured on streptavidin coated microtiter plates and detected calorimetrically by an alkaline phosphatase assay (Nickerson et al., 1990)

f. Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, that is extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

XI. Data Acquisition and Analysis

The PME system, including switching the lasers and collecting the data are under computer control in a unified hardware/software framework. Cross-platform versatility is achieved, for example, by using PCI-bus data acquisition and controller cards and LabView™ software from National Instruments. The graphically oriented acquisition and analysis environment provided by LabView has led to its widespread adoption in laboratory use. Software programs have been developed to perform several operations for the PME sequencing prototypes including: (i) generating a trigger signal for the TTL clock chip to govern the basic 4 sub-cycles (serial pulsing of lasers 1 through 4) of each cycle, (ii) controlling the blocking of scattered light, (iii) acquisition of the time-integrated signals from the photodetector, and (iv) controlling various operations for automated capillary electrophoresis methods. Scattered light is controlled by use of a liquid crystal tunable filter under electronic command (e.g., the VariSpec from CRI, Inc.) to provide a different edge block for each of the four lasers. When using a PMT or avalanche photodiode, sampling should be taken several times per sub-cycle for purposes of time-integration. For the full-scale multichannel CCD operation, only one read per sub-cycle is necessary. These different modes of operation are easily handled in software. As mentioned above, a primary goal of this invention is direct detection, which would eliminate the need for PCR amplification. This requires high direct sensitivity such as can be obtained with a spectroscopic-grade CCD camera with very low readout noise (e.g., a few accumulated photons per readout).

In addition, software programs that perform a number of data analysis steps, including spectral matrix correction, baseline correction, electrophoretic mobility corrections, base-calling of the single nucleotide, quantitation of peak heights for heterozygote analyses, allele association by electrophoretic position and order of different fluorescently labeled gene targeted primers are developed. Excitation by PME produces some level of cross-talk from the non-matched laser pulses other than from the best matched laser. As discussed previously, laser-dye combinations that minimize non-matched laser cross-talk can be easily identified, so that time correlated excitation of the correct fluorophore can be identified and made with high confidence. In general, however, it will be necessary to accommodate heterozygous base pairs, particularly for SNP analyses in which more than one fluorophore is excited at a time. Under non-saturating conditions, this leads to linear relations between the number $N_i$ of photons detected due to illumination by laser i and the number $n_j$ of molecules of dye j, $$N_i = \Sigma_j \alpha_{i,j} n_j$$

The matrix α implicitly contains factors including the molar extinction coefficients of the different dyes at frequency i, their quantum yields, the efficiencies of the laser and the detection system, and attenuation effects. From a practical point of view, the relative magnitudes of the elements $\alpha_{i,j}$ are calibrated experimentally. The matching of the dye maxima to the laser colors makes the matrix diagonally dominant, allowing it to be inverted without numerical difficulties. The inversion of α removes the residual cross-talk between the dyes. Thus it should be possible to directly obtain the relative numbers of dye molecules with maximum contrast from the four-color experiments. Corrections to this may come from scattered light. While a simple baseline correction is easily accommodated, light fluctuations will add some noise to the experiments. Several full cycles of the four lasers will pass during each elution component, allowing reduction of the noise by signal averaging. At the same time, the quantification of the noise provides a real-time diagnostic for estimating confidence levels on the signal measurements. Base-calls should in any case proceed with high confidence since the precise handling of the cross-talk will ordinarily yield one dye population that is much higher than the others. In those cases where heterozygotes are present, it is straightforward to distinguish these mixed-populations since they will yield two dyes with higher (and approximately equal) populations.

As used herein, the term "timing program" is meant to include either software or hardware configured to signal a laser firing sequence. The timing program will also contain information from the laser firing sequence, which can be correlated with the fluorescence emission signal.

As used herein, the term "excitation line" means a laser beam or output from another excitation source having a spectral wavelength or its corresponding frequency.

As used herein, the term "substantially all" means at least 90%. For example, "substantially all of the fluorescence signal" is at least 90% of the signal.

As used herein, the term "substantially corresponds" means that the difference between the two is less than 5%. For differences in wavelengths in the visible spectrum, this corresponds to differences of 20-33 nm, or more preferably 10-20 nm, or even more preferably 5-10 nm, or most preferably, when the absorption maxima of a dye "substantially corresponds" to the excitation wavelength of an excitation line, the two wavelengths are less than 5 nm.

As used herein, the term "optically matched" means that the wavelength maxima are within one nm of each other.

The term "substantially colinear" means that the laser beams or excitation lines diverge from each other at angles of less than 5°.

The term "substantially coaxial" means that the laser beams or excitation lines diverge from each other at angles of less than 5°.

The term "phased shifted," means that the phase relationship between two alternating quantities of the same frequency is changed. For example, consider two trains of repeating pulses such as pulse train (1) laser 1 on followed by laser 1 off for three times as long and pulse train (2) laser 2 on followed by laser 2 off for three times as long. One would say that the sequence of equal time periods of laser 1 on, laser 1 off, laser 2 on, laser 2 off corresponds to the sum of pulse train (1) and pulse train (2) with the phase of pulse train (2) delayed by a phase shift of 180° or a half cycle. Note that for 180°, delayed or advanced phase shifts are equivalent.

As used herein, the term an "on-time window" is defined as the window of time corresponding to when the excitation line is incident on the sample and includes the window of time corresponding to the time after the excitation line has ceased firing and before a second excitation line is incident on the sample.

As used herein the specification, "a" or "an" may mean one or more. As used herein in the claim(s), when used in conjunction with the word "comprising", the words "a" or "an" may mean one or more than one. As used herein "another" may mean at least a second or more.

XII. Examples

The following example is included to demonstrate preferred embodiments of the invention. It should be appreciated by those of skill in the art that the techniques disclosed in the examples which follow, represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Optical System

To test the concept of the PME system, a simple breadboard device was built to test the feasibility of discriminating different fluorescent signals from a mixture of two BODIPY fluorophores (Metzker et al., 1996). The optical path for combining the pulsed 532 nm and 635 nm lines is depicted schematically in FIG. 1 as solid lines. The laser light emitted from the green 532 nm solid state, diode-pumped, frequency-doubled Nd:YAG laser (Intelite, Minden, N.Y.) and the red 635 nm SPMT diode laser module with external potentiometer (Blue Sky Research, San Jose, Calif.) were each directed using two commercial grade aluminum steering mirrors (Edmund Industrial Optics, Barrington, N.J.) to a dual prism assembly. The prisms were coated with a single layer HEB-BAR antireflection material, which reduced polarization at the prism surfaces by increasing total transmittance. The high dispersion equilateral prisms were constructed from F2, grade "A" fine annealed flint glass and were positioned at a forty-five degree angle relative to one another to allow efficient overlap of the two beams by inverse dispersion into a single beam, FIG. 2. The flexibility of this design allows as many as eight excitation lines originating from discrete point sources (five lasers are shown in FIG. 1 for illustration) to be combined efficiently by the inverse dispersion strategy.

The combined laser beams were directed into the cuvette assembly box, which consists of a hollow aluminum light-proof box. The box was modified by affixing two "floating" adjustable iris fixtures (Edmund Industrial Optics) to minimize the amount of stray light entering the box. A 10 cm cylindrical optically correct glass cuvette (NSG Precision Cells, Inc, Farmingdale, N.Y.) was installed and mounted using two black delrin holders. A 500K multi-alkali PMT detector, which has good sensitivity in the range of 280 nm to 850 nm, was coupled to the cuvette assembly box. The fluorescence was detected directly from the cuvette using a collection lens in an orthogonal geometry to the propagation direction of the excitation laser beams.

Example 2

Pulse Generation System

Figure 3:
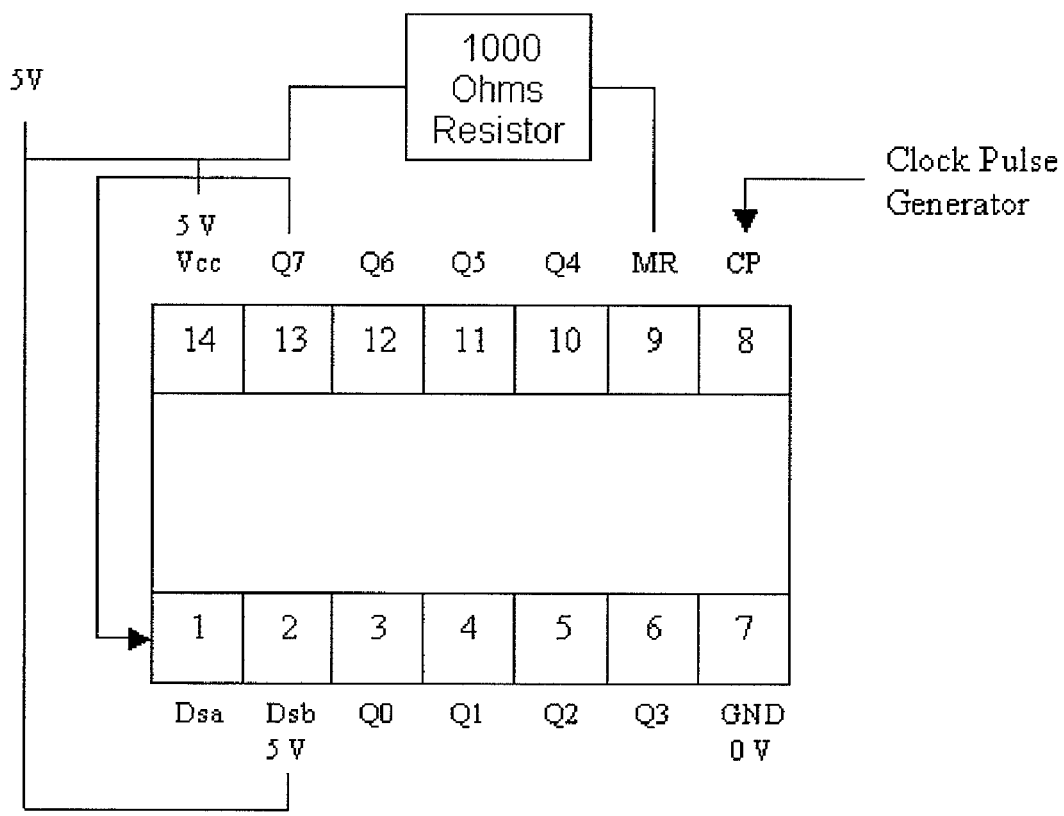
FIG. 3. TTL Circuit Clock Chip (74174). MR, when low, resets the chip and sets all outputs to low; CP is the Clock Pulse Input. Q0 through Q7 are outputs that connect to and signal each of up to eight lasers to fire in sequence.

There are a number of methods to serially pulse multiple lasers, including mechanical chopping and TTL control. One strategy was to serially pulse the 532 nm solid-state laser and the 635 nm diode laser by TTL control using 74174-clock chip, (FIG. 3). The advantages of the clock chip TTL circuit are its simplicity and flexibility as it is designed to pulse of up to eight discrete sources. As an alternative, a TTL bucket brigade circuit was constructed because of its simplistic design in pulsing 4-lasers using 2 dual J/K flip/flop chips. The TTL Clock Chip essentially provides a means for distributing the timing pulses from a master clock on the computer to the appropriate lasers. As each clock pulse is received, the chip output sequentially shifts one step from Q0 to Q1 . . . and finally to Q7 on the 8th clock pulse. Each laser is turned on in turn for one and only one clock pulse. The total cycle time may be easily varied by several orders of magnitude, from tens of seconds to milliseconds simply by changing the master clock frequency, and this has been successfully tested. The duration of the laser pulses are always identical to each other, and the off time between the pulses remain in the same exact proportion to each other, so the overall cycle time may be changed with a single parameter.

Example 3

Results and Discussion from the 2 Color PME Study

A preliminary experiment was performed to determine the feasibility of the PME approach to discriminate each fluorophore from a mixture of fluorescence dyes. To test the concept of "colorblind" detection, this experiment was performed without the aid of fluorescence band pass filters, laser line blocking filters, gratings, prisms, or any other dispersing elements to aid in distinguishing one dye's emission from the other. Moreover, the raw output from the photomultiplier was sent directly to an oscilloscope, without signal averaging or any other type of processing enhancement. Each laser was alternately pulsed for 1.2 msec and was configured with the red laser connected to Q0 and the green laser connected to Q3, FIG. 3. Altering the green laser to Q2 gave the correct firing sequence, which verified the proper configuration of the TTL circuit (data not shown). The remaining Q inputs were idle and resulted in dark spacing between laser pulses of 2.4 msec (red-to-green) and of 4.8 msec (green-to-red). The red and green lasers provided 5.5 mW and 4 mW of power, respectively. The difference in power settings was purposeful to partially offset the higher detector sensitivity of the green fluorescence over the red fluorescence. Photographs were taken by a digital camera in real time, and the fluorescent signals were recorded in a downward (negative) direction, as the PMT multiplies electrons.

The two dyes examined were BODIPY (523/547) and BODIPY (630/650), which have narrow absorption/emission half-bandwidths (Metzker et al., 1996), and therefore are ideal for the color-blind PME detection scheme. The dyes were analyzed at a concentration of approximately $10^{-5}$ M in ethanol. This moderately high concentration was chosen to assure that the signals were derived entirely from the dye solutions, and not from other sources, such as stray light, thus providing an accurate measure of the contrast ratio. The emission from each dye fell in toto onto the red-sensitive photomultiplier, which is a key feature of the color-blind methodology.

In FIG. 4A, the oscilloscope trace was obtained from an equal mixture of BODIPY dyes in the cuvette. The two channels from the oscilloscope photographs were set to record the trigger signal, which turns on the red laser (upper trace) and the fluorescence signal from the PMT detector (lower trace). The green laser pulse was subjected to a partial modulation, which gives the fluorescence output a "two-finger" appearance, making it easily distinguishable from the smooth red laser fluorescence. The small variation observed in the red laser pulse-to-pulse fluorescence intensity was due to 120 Hz leakage from an inadequately rectified AC power supply, and can be corrected by insertion of a capacitor $\pi$ filter in the power supply in the experimental section. As shown, the timing of the sequential firing of the red laser and then the green laser resulted in significant fluorescence signals when both BODIPY dyes were present in solution.

FIG. 4B shows the total fluorescence signal from the serial pulsing of the green and red lasers with only the BODIPY 630/650 (red dye) present in the cuvette. Whereas the large fluorescence signal is time correlated with the firing of the red laser, the green laser only imparts a small "cross-talk" signal to the red dye. This cross-talk was measured to be approximately 4% of the red laser signal, which is attributed to the highly efficient coupling of a laser precisely matched to the red dye absorption peak and the narrower absorption spectral properties of BODIPY dyes. Both aspects give the desired low excitation efficiency of the off-resonant green laser. This result clearly illustrates good contrast between laser excitations for the same dye using the PME approach. Since the ratio of red to green excitation efficiency can be determined, a cross-talk matrix can be computed and mathematically applied to yield a much higher contrast ratio.

FIG. 4C shows the total fluorescence signal from the serial pulsing of the red and green lasers with only the BODIPY 523/547 (green dye) present in the cuvette. The only fluorescence signal observed is time correlated with the firing of the green laser, which gives the "two-finger" signature. Unlike that of the BODIPY 630/650, the cross-talk signal observed from the red laser is negligible on this scale, and further signal amplification revealed it to be considerably less than 1% of that from the green laser. This observation is expected because longer wavelength excitation sources should not impose photon absorption on shorter wavelength dyes (i.e., the red laser does not excite the green dye). This feature illustrates an important and key advantage of reduced cross-talk of fluorophores using the PME strategy. Consider a four dye system, which is made-up of blue, green, yellow, and red dyes. The blue dye should not exhibit cross-talk from the sequential firing of the green, yellow, and red lasers. The green dye, on the other hand, will exhibit cross-talk from the only blue laser, but not the yellow or red lasers. The yellow dye will exhibit cross-talk from the blue and green lasers, but not the red laser and so forth. In other words, the observed cross-talk on the "blue" portion of the spectrum relative to the absorption/excitation maxima of a given dye is negated, which is significantly different from emission cross-talk of blue green, yellow, and red dyes excited using a single excitation source.

An excellent contrast ratio for the discrimination of two different BODIPY dyes using the PME technology by detecting all of the fluorescence emission in a true color-blind fashion is demonstrated. The experiment was designed using no spectral filtering elements of any kind, and the signal was taken directly from the oscilloscope in real time without signal averaging or other processing. These data show that the choice of experimental conditions provided significant fluorescence signal for which scattered laser light signals are negligible. Therefore, the 25:1 contrast ratio observed for this unaveraged raw signal obtained with laser pulses on the msec timescale provides a genuine comparison of the time correlated fluorescence detection technique.

Prophetic Example 4

Development of a 1-Capillary 4-Color PME Prototype a. Develop 4-Color: Identification of the Optimal 4 Laser-Dye Combination Six different solid-state lasers and/or laser diode modules have been identified with excitation wavelengths that match the absorption maxima of a number of commercially available fluorophores, most of which have been used for DNA sequencing. Other lasers and fluorophores can also be identified by comparing and matching the excitation maxima of the fluorophore with the emission wavelength of the laser. Candidate dyes should show good quantum yields and have narrow absorption spectra. The non-limiting list of dyes listed herein below initially meet these requirements, although other commercially available fluorophores and lasers may be tested as well. For experimentation purposes, each dye is coupled to the universal sequencing primer (5'-TTG-TAAAACGACGGCCAGT) (Metzker et al., 1996) (Sequence ID No.1) as representative of termination products for the SNP assay.

TABLE 1

| Laser | Fluorophore |
|---|---|
| Blue 399 nm solid state, indium gallium nitride laser | 7-dimethylaminocoumarin (409/473), cascade blue (396/410), and 7-hydroxycoumarin (386/448). |
| Blue 473 nm or 488 nm solid state, diode-pumped, frequency-doubled Nd:YAG laser | 5-carboxyfluorescein (494/518), 1,3,5,7-tetramethyl-BODIPY (495/503), Oregon green 488 (496/524), and the 5,7-dimethyl-BODIPY (503/512).* |
| Green 532 nm solid state, diode-pumped, frequency-doubled Nd:YAG laser | BODIPY (523/547) (536/554 when coupled to a primer) |
| Yellow 594 nm He—Ne | BODIPY 589/617 and BODIPY 581/591 (592/603 when coupled to a primer) |
| Red 635 nm SPMT diode laser module with external potentiometer | BODIPY 630/650 (643/651 when coupled to a primer) |
| Red 670 nm SPMT diode laser module with external potentiometer | The BODIPY (650/665) dye (661/667 when coupled to a primer) and cyanine 5 dye |

Although some dyes listed in Table 1 have a listed absorption maxima on the blue side of the excitation source, these dyes will be considered for use since the attachment of dyes to DNA usually results in a red shift in the absorption/emission spectra. The absorption/emission values for the dyes given in parenthesis correspond to the absorption and emission wavelengths when coupled to a universal sequencing primer.

A systematic evaluation of each laser-dye combination will be compared for good excitation characteristics and between laser-dye pairs to identify an optimal set of 4 laser-dyes for DNA sequencing applications. Each laser will be set-up, similar to the green and red laser experiment and pulsed using the TTL clock chip for excitation and cross-talk experiments as described in Example 3. It is anticipated that numerous new solid-state lasers and laser diodes and new fluorescent dyes will continue to be developed and commercialized with unique emission wavelengths ranging below 400 nm to beyond 1100 nm that can be used in the current invention. Due to the modular configuration of the PME system, the testing of additional laser-dye pairs is straightforward.

b. Construction of the 1-Capillary Breadboard Prototype

A 1-capillary electrophoresis unit will be set-up on a breadboard platform, and the electrophoresis will be driven initially using a 30 kV power supply. A Plexiglas box equipped with a safety interlock will be constructed to enclose the samples and the running buffers. Initially, electrophoresis will be performed under ambient conditions due to the nature of the short primer extension products; however, a temperature controlled heating jacket to improve electrophoretic resolution will be constructed if necessary. The separation format will use fused silica capillaries (150 μM OD, 50 μM ID, and 50 cm in length), POP-6 solution as the separation matrix, and TBE as the running buffer. A 1-capillary sheath flow cuvette will be constructed using the rectangular, tapered design described by Zhang et al. (1999) and sheath flow will be driven by syringe pump at a flow rate of approximately 0.3 mL per hour.

c. Sensitivity Experiments for Direct Detection

Although limited sensitivity information can be obtained from the 2-color PME system (FIG. 1), more data will be obtained from conducting sensitivity experiments directly using the 1-capillary instrument. Subsequent to the identification of the 4 laser-dye set, but overlapping with the construction of the 1-capillary instrument, the PME laser system will be coupled to the electrophoresis device. For limit of detection assays, both the PMT and the silicon APD (current and counting modes) will be investigated over a wide range of fluorophore-labeled universal primer concentrations. Sensitivity assays will be conducted using free zone and POP-6-based capillary electrophoresis. A unique feature of the PME system is that limit of detection experiments will be performed for the 4 laser-dye sets identified previously. It should be noted that limit of detection experiments are only informative regarding sensitivity when the test dye is optimally excited and producing maximum fluorescence signal. Sensitivity experiments are not possible or practical using all four fluorophores with the standard spectrally resolved DNA sequencing systems because the longer wavelength dyes are inefficiently excited. Therefore, the limit of detection experiments typically published in the literature are performed using the dye most closely matched to the laser source (out of the set of four), which is usually fluorescein and the argon ion laser (Swerdlow et al., 1990; Drossman et al., 1990; Swerdlow et al., 1990; Zhang et al., 1999). Here, limit of detection experiments will be performed using all four PME fluorophores because the lasers are closely matched for optimal excitation and therefore will produce a more robust picture for sensitivity with respect to the entire sequencing chemistry.

d. Development of Rapid Sample Preparation Methods for Direct Fluorescent Assays from Genomic DNA The PME instrument should be able to detect as few as $10^4$-to-$10^5$ fluorescent molecules. Given that 1 mL of whole blood contains approximately $10^6$ white blood cells, direct detection (without the need for amplification of the sample) of multiple SNPs is possible. Initially, SNP assays will be performed using standard PCR techniques and diluted appropriately to simulate direct genomic DNA levels. This approach will allow the performance of limit of detection experiments without dependence or delay for the development of optimized sample preparation methods and direct genomic SNP assays.

Sample preparation methods will be developed from whole blood to be fast, simple, and amenable to direct single nucleotide primer extension assays. Typically, most methods involve the fractionation of whole blood into serum, red blood cells, and white blood cells, of which the latter is used for analysis. Sample preparation experiments can rely on commercially available kits and published protocols for evaluation and optimization.

As discussed hereinabove, sequencing assays are typically performed in μL quantities, but loaded onto commercial capillary electrophoresis instruments in nL quantities. To minimize wasting direct assay samples, reaction volume assays will be optimized in a target volume of 1 μL. Since electrokinetic injection will be implemented as the injection method for each prototype, injection biases will most likely occur depended on sample purity (Huang et al., 1988). Therefore, several solid-phase and affinity-based purification schemes will be investigated for producing highly purified fluorescently labeled SNP assays, which are devoid of contaminants, such as unincorporated fluorescent terminators, salts, and other electro-competing macromolecules.

In the event that the sensitivity limit of the PME technology is several orders of magnitude higher than anticipated (i.e., $10^6$-to-$10^7$ fluorescent molecules), direct detection from whole blood can still be achieved. This can be done by increasing the amount of blood analyzed from 1-to-10 mL, and/or performing a linear amplification of the primer extension assay by temperature cycling, typically used in Sanger sequencing reactions.

Prophetic Example 5

Construction of a Portable 8-Capillary PME DNA Sequencer a. Construction of 8-APD Detector for a Portable System A PME DNA sequencer that is portable will be useful for any applications where there are space limitations or where it is important to be able to move the sequencer. The technology to modify the PME DNA sequencer such that it is portable is currently available. For the portable DNA sequencer, the optical system developed for the breadboard will be adapted to become more compact and robust. The highly efficient dual prism combiner will be initially adapted to the portable sequencer. Constructed with microbench components, the optics train will be incorporated into a 4-rail structure, which was developed for the very rigid needs of laser cavity mirror supports. The commercially available miniature 4-rail system will also be used to support the sheath flow cuvette and collection optics. As previously discussed, commercial diode laser modules are remarkably compact, typically 1" or 2" long, and are generally available with optical fiber coupled outputs. Fiber splitter/combiners have been developed for laser based communications, and contingent on this rapidly emerging technology, it may be feasible to combine the beams and deliver the 4-laser sources to the sheath flow cuvette in a single optical fiber. For this design, only a conventional achromatic lens will be needed to project the collimated alternating multicolor beam through the sheath flow cuvette.

A wide field f/1 (NA ~0.5) lens will be used to collect the fluorescent light from the capillary plumes and project it onto 8 APDs. A microscope objective is often used for this purpose, but may suffer vignetting and consequent loss of fluorescence signal from the outermost capillary plumes. The lens mount will be equipped with opposing adjustment screws that lock the lens into place after optimization. The light path will be shielded with baffles to reduce scattered laser light reaching the detectors. An optional liquid crystal device will be used as an edge filter to block scattered laser light, as needed; this device has a rejection ratio of about 4 orders of magnitude. Unlike the familiar rotating filter wheel, the liquid crystal device has no mechanical moving parts. The liquid crystal filter has a response time of several milliseconds, so that it will be cycled under computer control along with the 4 lasers, blocking scattered light from each one in turn, while passing essentially all of the fluorescent light to the color blind APD detectors.

Although it is preferable to imaged fluorescent light directly onto the APDs, the collection lens, which typically magnifies the image 20× may not be enough to resolve 8 images for detection. One solution is to use a small mirror or prism affixed to each APD housing, which can deflect the beam at right angles. This design can be mounted in a staggered array and thereby reduce this congestion. Individual gradient refractive index (GRIN) lenses and optical fiber couplings to each APD will also be considered in the portable configuration. However, the insertion loss for a properly coated beam steering prism is about 2%, and it is most unlikely that the fiber coupling will perform as well. This fiber coupling problem is much more significant for the projected fluorescent image, which behaves as an extended source, than it is for a laser beam. Finally, the same rigid 4-rail structure mentioned above will be used to support the detection system.

The laser and TTL circuit power supplies typically have a footprint of a few square inches, and the power supplies for the APDs and the 10 kV electrophoresis modules are slightly larger, but still only a few inches long. These various electronic components will be easily positioned beneath and around the capillaries, which will travel around the perimeter of the system, thus avoiding sharp bends.

b. PME of Residual Signal

Residual fluorescence may be detected immediately after very short excitation laser pulses have irradiated the sample. With such an approach, the lasers will be off during the period that the fluorescent signal is collected. This may be particularly important for the development of sequencing on a chip, because the chip almost inevitably will generate large amounts of scattered light.

Specifically the intent is to sequentially fire pico-second laser pulses at a fluorescently labeled DNA sample and then "look" for a fluorescent response on the nanosecond time-scale, immediately after the laser pulse ends. This novel approach is a logical extension to the central principle of operation intrinsic to the core PME technology. This innovative experimental strategy is referred to as "Looking In The Dark" or "PME-LITD".

The primary advantage of the Looking In The Dark strategy is the complete elimination of scattered light, which at low levels of fluorescence is likely to be a main source of noise in the PME instrument. This technique, if successful, could have enormous implications for improving the signal-to-noise ratio and potentially improve the overall sensitivity of the instrument.

The following example details a simple sequence of events to illustrate the PME-LITD concept:

1. The first laser in sequence is pulsed for 50 pico-seconds.
2. A 500 pico-second time delay is applied after the laser has been switched off. Note that during the delay period no fluorescence is sampled by the detector.
3. A fast photon counter is used to look for any fluorescent response from the labeled DNA during the ensuing 50 nano-second gated window.
4. Steps 1 through 3 are repeated in sequence for each laser in the subcycle.
5. The pico-second pulsed excitation and nano-second gated detection windows cycle continuously.

For a four color system, the above steps would generate a subcycle time that is 202.2 nanoseconds. This implies that over an eight second time window, (approximate time for a labeled DNA band to pass through an ABI 3700 cuvette), around 40 million complete subcycles would be completed. The data collected will then be appropriately averaged and further processed to yield high quality analyzed data.

To conduct these types of experiments, lasers that are capable of generating very short pulses of sub-nanosecond duration will be required. Pico-second laser sources are commercially available from a number of companies including Coherent Laser Group, Newport, and PicoQuant. For example, Coherent has a diode pumped mode-locked laser with fundamental wavelengths at either 1047 nm, 1053 nm or 1064 nm, which generates pulses as short as 2 ps. The second harmonics can easily be generated from picosecond sources, hence the following wavelengths would be available: 532 nm, 526.5 nm, and 523.5 nm. Newport also manufactures a "NanoLaser" that generates sub-nanosecond green, (532 nm) light, at an average power of more than 6 mW.

In addition, an instrument that is capable of counting photons on a sub-nanosecond time scale will also be needed; such devices are available from a variety of manufacturers. For example, "FAST ComTec" produces a single photon counting instrument, which has resolution on the time-scale of 500 pico-seconds. Becker & Hickl GmbH also manufactures a four channel correlated single photon counting device that has resolution down to 813 femto-seconds. Furthermore, it should be noted that when coupled into an appropriately configured electronic circuit the recovery time of a silicon avalanche photo-diode detector, (following illumination by scattered light from a excitation laser pulse), is of the order of 500 pico-seconds. This rapid recovery time will permit the effective observation of fluorescence from a dye with a fluorescent lifetime of several nanoseconds in the complete absence of any laser excitation, i.e. "in the dark".

Four wavelengths can be generated from a single laser, as opposed to using four synchronized and mode-locked lasers. This can be done using Stimulated Raman Shifting, (SRS).

An experiment to test the PME-LITD strategy comprises a simple two-color system. Specifically, a mode-locked Nd:YAG laser generating 50 pico-second pulses will be coupled to a Raman cell filled with molecular nitrogen. The superimposed multi-wavelength output from the Raman cell will be then dispersed and ultimately recombined using a four-prism assembly. In the middle of the four-prism assembly, (i.e. where the various excitation lines are separated and traveling approximately in parallel), a pair of electro-optic modulators will be used to chop the colored pulses—selecting alternate pulses from each beam. The recombined beams will then be directed into a cuvette assembly—similar to the prototype described in FIG. 1. Finally, the time-resolved fluorescence will be detected using a fast photon counter that looks for photons in a window that spans the range from 0.5 ns-50.5 ns after the cessation of each laser pulse.

c. Construction of a 96-Capillary PME Suitcase DNA Sequencer

A portable 96-capillary PME DNA sequencer is envisioned as an aspect of the current invention. In one embodiment, the four-laser illumination system described in the 8-capillary sheath flow cuvette system will be used for the 96 capillary system. All four alternating excitation lines will be coaxial and well collimated to facilitate the illumination of the 96 fluorescent plumes. Although the compact multi-laser source will remain unchanged, it will not be practical to scale the detection system from 8 APDs to 96 discrete detectors. A CCD camera, however, will be more suited to perform this operation. A fast lens such as f/1, with good imaging quality will be installed for efficient light collection. A second lens will be used to re-image the light onto the CCD. The computer-controlled liquid crystal filter may be interposed between the two lenses to block scattered laser light, if needed. Baffles will be used to minimize stray light, but there are no restricting apertures that reduce the wide cone angle of collection, or dispersing elements that further attenuate the signal.

Essentially all of the fluorescent light from one sheath flow plume will fall on one particular group of pixels, and these pixels are binned together so they are read out as a single unit, which will reduce readout noise. Binning of all of the fluorescence from a capillary into effectively one giant pixel provides a single robust signal from each capillary plume even when the amount of fluorescing dye is quite small.

The CCD camera is quite compact, and even with adding thermoelectric cooling to reduce background noise, fitting the CCD detector into a compact device will not be problematic. A portable computer will read out the CCD contents at the end of each laser pulse. For a standard video rate of 30 Hz, the entire cycle frequency of 4 lasers will be 7.5 Hz (5 Hz with the incorporation of a liquid crystal laser blocker), and this will allow for the data from dozens of readout cycles to be signal averaged per one elution event. Following the construction of the CCD suitcase system, detailed limit of detection experiments will be performed to compare it to the performance of the 8-capillary APD suitcase prototype.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Anazawa, T, S Takahashi, and H Kambara (1996) A capillary array gel electrophoresis system using multiple laser focusing for DNA sequencing. Anal. Chem. 68: 2699-2704.

Barany, F (1991) Genetic disease detection and DNA amplification using cloned thermostable ligase. Proc. Natl. Acad. Sci. USA 88:189-193.

Brenner S, M Johnson, J Bridgham, G Golda, D H Lloyd, D Johnson, S Luo, S McCurdy, M Foy, M Ewan, R Roth, D George, S Eletr, G Albrecht, E Vermaas, S R Williams, K Moon, T Burcham, M Pallas, R B DuBridge, J Kirchner, K Fearon, J Mao, and K Corcoran. (2000) Gene expression analysis by massively parallel signature sequencing (MPSS) on microbead arrays. Nat. Biotechnol. 18:630-634.

Cohen A S, D R Najarian, and B L Karger (1990) Separation and analysis of DNA sequence reaction products by capillary gel electrophoresis. J. Chromatogr. 516:49-60.

Crabtree H J, S J Bay, D F Lewis, J Zhang, L D Coulson, G A Fitzpatrick, S L Delinger, D J Harrison, and N J Dovichi (2000) Construction and evaluation of a capillary array DNA sequencer based on a micromachined sheath-flow cuvette. Electrophoresis 21:1329-1335.

Deeb S S, L Fajas, M Nemoto, J Pihlajamaki, L Mykkanen, J Kuusisto, M Laakso, W Fujimoto, and J Auwerx (1998) A Pro12Ala substitution in PPARγ2 associated with decreased receptor activity, lower body mass index and improved insulin sensitivity. Nature Genet. 20:284-287.

Drossman H, J A Luckey, A J Kostichka, J D'Cunha, and L M Smith. (1990) High-speed separations of DNA sequencing reactions by capillary electrophoresis. Anal. Chem. 62:900.

Effenhauser, et al Anal. Chem., 66:2949-2953, 1994.
Effenhauser, et al. Anal. Chem., 65:2637-2642, 1993.
Harrison et al., Science, 261:895-897, 1993.

Huang X, M J Gordon, and R N Zare (1988) Bias in quantitative capillary zone electrophoresis caused by electrokinetic sample injection. Anal. Chem. 60:375-377.

Huang X C, M A Quesada, and R A Mathies. (1992) Capillary array electrophoresis using laser-excited confocal fluorescence detection: an approach to high-speed, high-throughput DNA sequencing. Anal Chem. 64:967-972.

Huang X C, M A Quesada, and R A Mathies. (1992) DNA sequencing using capillary array electrophoresis. Anal Chem. 64:2149-2154.

Ju J, C Ruan, C W Fuller, A N Glazer, and R A Mathies (1995) Fluorescence energy transfer dye-labeled primers for DNA sequencing and analysis. Proc. Natl. Acad. Sci. USA. 92:4347-4351.

Kambara H and Takahashi S. (1993) Multiple-sheathflow capillary array DNA analyser. Nature 361: 565-566.

Karger A E, J M Harris, and R F Gesteland. (1991) Multiwavelength fluorescence detection for DNA sequencing using capillary electrophoresis. Nucleic Acids Res. 19:4955-4962.

Kheterpal I, J R Scherer, S M Clark, A Radhakrishnan, J Ju, C L Ginther, G F Sensabaugh, and R A Mathies (1996) DNA sequencing using a four-color confocal fluorescence capillary array scanner. Electrophoresis 17:1852-1859.

Kornher, J S and K J Livak (1989) Mutation detection using nucleotide analogs that alter electrophoretic mobility. Nucleic Acids Res. 17:7779-7784.

Kuppuswamy, M N, J W Hoffmann, C K Kasper, S G Spitzer, S L Groce and S P Bajaj (1991) Single nucleotide primer extension to detect genetic diseases: Experimental application to hemophilia B (factor IX) and cystic fibrosis genes. Proc. Natl. Acad. Sci. (U.S.A.) 88:1143-1147.

Kurg A, Tonisson N, Georgiou I, Shumaker J, Tollett J, Metspalu A., "Arrayed primer extension: solid-phase four-color DNA resequencing and mutation detection technology." Genet Test 2000; 4(1):1-7

Landegren U, R Kaiser, J Sanders, and L Hood. (1988) A ligase-mediated gene detection technique. Science 241: 1077-1080.

Lee J S, and M Anvret. (1991) Identification of the most common mutation within the porphobilinogen deaminase gene in Swedish patients with acute intermittent porphyria. Proc Natl Acad Sci USA. 88:10912-10915.

Lieberwirth U, J Arden-Jacob, K H Drexhage, D P Herten, R Muller, M Neumann, A Schulz, S Siebert, G Sagner, S Klingel, M Sauer, and J Wolfrum. (1998) Multiplex dye DNA sequencing in capillary gel electrophoresis by diode laser-based time-resolved fluorescence detection. Anal Chem. 70:4771-4779.

Livak K J and J W Hainer. (1994) A microtiter plate assay for determining apolipoprotein E genotype and discovery of a rare allele. Hum Mutat. 3:379-385.

Lu X and E S Yeung. (1995) Optimization of excitation and detection geometry for multiplexed capillary array electrophoresis of DNA fragments. Appl. Spectrosc. 49: 605-609.

Luckey J A, H Drossman, A J Kostichka, D A Mead, J D'Cunha, T B Norris, and L M Smith. (1990) High speed DNA sequencing by capillary electrophoresis. Nucleic Acids Res. 18:4417-4421.

Luryi, S. CRISP Abstract: Grant Number 5R01HG01487-05. 4 Color automated DNA sequencing machine with asynchronous network operation.

Madabhushi R S (1998) Separation of 4-color DNA sequencing extension products in noncovalently coated capillaries using low viscosity polymer solutions. Electrophoresis 19:224-230.

Manz, et al., J. Chromatogr., 593:253-258, 1992.

Meaburn, J (1976) "Detection and Spectrometry of Faint Light", D. Reidel, Dordrecht, Holland.

Metzker M L, J Lu, and R A Gibbs (1996) Electrophoretically uniform fluorescent dyes for automated DNA sequencing. *Science* 271:1420-1422.

Metzker M L, R Raghavachari, S Richards, S E Jacutin, A Civitello, K Burgess, and R A Gibbs. (1994) Termination of DNA synthesis by novel 3'-modified-deoxyribonucleoside 5'-triphosphates. *Nucleic Acids Res.* 22:4259-4267.

Nickerson D A, R Kaiser, S Lappin, J Stewart, L Hood, and U Landegren. (1990) Automated DNA diagnostics using an ELISA-based oligonucleotide ligation assay. *Proc Natl Acad Sci USA.* 87:8923-8927.

Nikiforov T T, R B Rendle, P Goelet, Y H Rogers, M L Kotewicz, S Anderson, G L Trainor, and MR Knapp. (1994) Genetic Bit Analysis: a solid phase method for typing single nucleotide polymorphisms. *Nucleic Acids Res.* 22:4167-4175.

Nyren P, B Pettersson, and M Uhlen (1993) Solid phase DNA minisequencing by an enzymatic luminometric inorganic pyrophosphate detection assay. *Anal Biochem.* 208:171-175.

Prezant T R, and N Fischel-Ghodsian. (1992) Trapped-oligonucleotide nucleotide incorporation (TONI) assay, a simple method for screening point mutations. *Hum Mutat.* 1:159-164.

Prober J M, G L Trainor, R J Dam, F W Hobbs, C W Robertson, R J Zagursky, A J Cocuzza, M A Jensen, and K Baumeister. (1987) A system for rapid DNA sequencing with fluorescent chain-terminating dideoxynucleotides. *Science* 238:336-341.

Quesada M A and S Zhang (1996) Multiple capillary DNA sequencer that uses fiber-optic illumination and detection. *Electrophoresis* 17:1841-1851.

Quesada M A, H S Dhadwal, D Fisk, and F W Studier (1998) Multi-capillary optical waveguides for DNA sequencing. *Electrophoresis* 19:1415-1427.

Ronaghi M, M Uhlen, and P Nyren. (1998) A sequencing method based on real-time pyrophosphate. *Science* 281: 363-365.

Rosenblum B B, L G Lee, S L Spurgeon, S H Khan, S M Menchen, C R Heiner, and S M Chen. (1997) New dye-labeled terminators for improved DNA sequencing patterns. *Nucleic Acids Res.* 25:4500-4504.

Sambrook et al, "Molecular Cloning," *A Laboratory Manual*, 2d Ed., Cold Spring Harbor Laboratory Press, New York, 13.7-13.9:1989.

Shibata K, M Itoh, K Aizawa, S Nagaoka, N Sasaki, P Caminci, H Konno, J Akiyama, K Nishi, T Kitsunai, H Tashiro, M Itoh, N Sumi, Y Ishii, S Nakamura, M Hazama, T Nishine, A Harada, R Yamamoto, H Matsumoto, S Sakaguchi, T Ikegami, K Kashiwagi, S Fujiwake, K Inoue, and Y Togawa (2000) RIKEN integrated sequence analysis (RISA) system-384-format sequencing pipeline with 384 multicapillary sequencer. *Genome Res.* 10:1757-1771.

Shumaker J M, A Metspalu, and C T Caskey. (1996) Mutation detection by solid phase primer extension. *Hum Mutat.* 7:346-54.

Smith L M, J Z Sanders, R J Kaiser, P Hughes, C Dodd, C R Connell, C Heiner, S B Kent, and L E Hood (1986) Fluorescence detection in automated DNA sequence analysis. *Nature* 321:674-679.

Sokolov, B P (1990) Primer extension technique for the detection of single nucleotide in genomic DNA. *Nucleic Acids Res.* 18:3671.

Sweedler J V, J B Shear, H A Fishman, R N Zare, and R H Scheller (1991) Fluorescence detection in capillary zone electrophoresis using a charge-coupled device with time-delayed integration. *Anal. Chem.* 63:496-502.

Swerdlow H and R Gesteland (1990) Capillary gel electrophoresis for rapid, high resolution DNA sequencing. *Nucleic Acids Res.* 18: 1415-1419.

Swerdlow H, J Z Zhang, D Y Chen, H R Harke, R Grey, S L Wu, N J Dovichi, and C Fuller. (1991) Three DNA sequencing methods using capillary gel electrophoresis and laser-induced fluorescence. *Anal Chem.* 63:2835-2841.

Swerdlow H, SL Wu, H Harke, and N J Dovichi. (1990) Capillary gel electrophoresis for DNA sequencing. Laser-induced fluorescence detection with the sheath flow. *J. Chromatogr.* 516:61-67.

Syvanen, A C, K Aalto-Setala, L Harju, K Kontula, and H Soderlund. (1990) A primer-guided nucleotide incorporation assay in the genotyping of Apolipoprotein E. *Genomics* 8:684-692.

Takahashi, S, M Katsuhiko, T Anazawa, and H Kambara. (1994) Multiple sheath-flow gel capillary-array electrophoresis for multicolor fluorescent DNA detection. *Anal. Chem.* 66: 1021-1026.

Taylor J A and E S Yeung. (1993) Multiplexed fluorescence detector for capillary electrophoresis using axial optical fiber illumination. *Anal. Chem.* 65: 956-960.

Tsuda et al, *Anal. Chem.*, 62:2149-2152, 1990.

U.S. Pat. No. 4,582,788
U.S. Pat. No. 4,656,127
U.S. Pat. No. 4,683,194
U.S. Pat. No. 4,683,202
U.S. Pat. No. 5,296,375
U.S. Pat. No. 5,304,487
U.S. Pat. No. 5,784,157
U.S. Pat. No. 5,846,710
U.S. Pat. No. 5,856,174
U.S. Pat. No. 5,888,819
U.S. Pat. No. 5,904,824
U.S. Pat. No. 5,991,082
U.S. Pat. No. 6,004,744
U.S. Pat. No. 6,013,431
U.S. Pat. No. 6,038,023
U.S. Pat. No. 6,139,800
U.S. Pat. No. 6,153,379
U.S. Pat. No. 6,215,598
U.S. Pat. No. 6,226,126

Ueno K and E S Yeung (1994) Simultaneous monitoring of DNA fragments separated by electrophoresis in a multiplexed array of 100 capillaries. *Anal. Chem.* 66: 1424-1431.

Wei J, and G P Hemmings G P (2000) The NOTCH4 locus is associated with susceptibility to schizophrenia. *Nature Genet.* 25:376-377.

Woolley and Mathies, *Proc Natl Acad Sci USA*, 91:11348-52 1994.

Yeo G S, I S Farooqi, S Aminian, D J Halsall, R G Stanhope, and S O'Rahilly (1998) A frameshift mutation in MC4R associated with dominantly inherited human obesity. *Nature Genet.* 20:111-112.

Zagursky R J and R M McCormick. (1990) DNA sequencing separations in capillary gels on a modified commercial DNA sequencing instrument. *Biotechniques* 9: 74-79.

Zhang J, K O Voss, D F Shaw, K P Roos, D F Lewis, J Yan, R Jiang, H Ren, J Y Hou, Y Fang, X Puyang, H Ahmadzadeh, and N J Dovichi. (1999) A multiple-capillary electrophoresis system for small-scale DNA sequencing and analysis. *Nucleic Acids Res.* 27: e36.

What is claimed is:

1. A method of identifying sample components comprising:
   (a) obtaining a biological sample;
   (b) labeling said sample with one or more fluorophores;
   (c) separating components of said sample; and
   (d) detecting said sample components with a device wherein said device comprises:
      one or more lasers configured to emit two or more excitation lines, each excitation line having a different excitation wavelength;
      a timing circuit coupled to the one or more lasers and configured to fire the two or more excitation lines sequentially according to a timing program that pulses the one or more lasers on and off in a firing sequence to produce time-correlated fluorescence emission signals from the sample; and
      a non-dispersive detector positioned to collect the time-correlated fluorescence emission signals;
   wherein said detector collects time correlated data from said sample comprising fluorescent emissions of the sample as a result of irradiation by the one or more excitation lines.

2. The method of claim 1, wherein said sample components are nucleic acids.

3. The method of claim 1, wherein said sample components are amino acids.

4. The method of claim 1, wherein said sample components are proteins.

5. The method of claim 1, wherein said separating is by electrophoresis.

6. The method of claim 1, wherein said separating is by chromatography.

7. The method of claim 1, wherein said separating is by mass spectrometry.

8. The method of claim 1, wherein said sample components are addressed on high density chip arrays.

9. The method of claim 1, further comprising:
   (e) contacting said sample components on a surface comprising immobilized oligonucleotides at known locations on said surface; and
   (f) performing a single nucleotide incorporation assay.

10. The method of claim 1, further comprising:
    (e) contacting said sample components on a surface comprising immobilized oligonucleotides at known locations on said surface; and
    (f) performing a mini-sequencing assay.

11. The method of claim 9, further comprising rastering said surface or said excitation lines such that said excitation lines contact said surface at multiple locations.

* * * * *

SEQUENCE LISTING

<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: Synthetic primer

<400> SEQUENCE: 1
ttgtaaaacg acggccagt                                                19